(12) United States Patent
Punyani et al.

(10) Patent No.: US 10,561,591 B2
(45) Date of Patent: *Feb. 18, 2020

(54) HAIR CARE REGIMEN USING COMPOSITIONS COMPRISING MOISTURE CONTROL MATERIALS

(71) Applicant: The Procter & Gamble Company, Cincinnati, OH (US)

(72) Inventors: Supriya Punyani, Singapore (SG); Lisa Jo Bartz, Singapore (SG); Brian Xiaoqing Song, Mason, OH (US); Jennifer Mary Marsh, Deerfield Township, OH (US); Erica Vincil Buckner, Singapore (SG); Tiffany Tien-Yun Yang, Loveland, OH (US); Christina Marie Gemmer, Lebanon, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/367,363

(22) Filed: Dec. 2, 2016

(65) Prior Publication Data

US 2017/0157011 A1 Jun. 8, 2017

Related U.S. Application Data

(60) Provisional application No. 62/263,166, filed on Dec. 4, 2015.

(51) Int. Cl.
*A61K 8/365* (2006.01)
*A61K 8/44* (2006.01)
(Continued)

(52) U.S. Cl.
CPC .............. *A61K 8/466* (2013.01); *A61K 8/042* (2013.01); *A61K 8/342* (2013.01); *A61K 8/345* (2013.01);
(Continued)

(58) Field of Classification Search
None
See application file for complete search history.

(56) References Cited

U.S. PATENT DOCUMENTS

| 2,392,314 A | 1/1946 | Dalton |
| 4,329,097 A | 5/1982 | Steele et al. |

(Continued)

FOREIGN PATENT DOCUMENTS

| DE | 19536423 A1 | 4/1996 |
| DE | 1020011089357 A1 | 8/2012 |

(Continued)

OTHER PUBLICATIONS

"De-Frizz Leave-In Treatment", Quality Collor Cosmeticos, May 1, 2014, Mintel.

(Continued)

*Primary Examiner* — Kyung S Chang
(74) *Attorney, Agent, or Firm* — Linda M. Sivik

(57) ABSTRACT

A method is disclosed for reducing hair frizz by treating hair with a regimen comprising two or more hair care compositions wherein at least two of such compositions comprise Moisture Control Materials. Two or more of the compositions used in the method comprise from about 0.1% to about 20% of a moisture control material or mixture of moisture control materials wherein the moisture control material is selected from the group consisting of Class I and Class II.

31 Claims, 1 Drawing Sheet

(51) Int. Cl.

| | | |
|---|---|---|
| *A61Q 5/06* | (2006.01) | |
| *A61Q 5/12* | (2006.01) | |
| *A61Q 5/02* | (2006.01) | |
| *A61K 8/362* | (2006.01) | |
| *A61K 8/368* | (2006.01) | |
| *A61K 8/46* | (2006.01) | |
| *A61K 8/04* | (2006.01) | |
| *A61K 8/34* | (2006.01) | |
| *A61K 8/36* | (2006.01) | |
| *A61K 8/37* | (2006.01) | |
| *A61K 8/42* | (2006.01) | |
| *A61K 8/73* | (2006.01) | |
| *A61K 8/81* | (2006.01) | |

(52) U.S. Cl.
CPC .............. *A61K 8/361* (2013.01); *A61K 8/362* (2013.01); *A61K 8/368* (2013.01); *A61K 8/37* (2013.01); *A61K 8/42* (2013.01); *A61K 8/731* (2013.01); *A61K 8/817* (2013.01); *A61Q 5/02* (2013.01); *A61Q 5/06* (2013.01); *A61Q 5/12* (2013.01); *A61K 2800/5426* (2013.01); *A61K 2800/594* (2013.01); *A61K 2800/596* (2013.01); *A61K 2800/884* (2013.01)

(56) References Cited

U.S. PATENT DOCUMENTS

| | | |
|---|---|---|
| 4,496,536 A | 1/1985 | Moller et al. |
| 4,536,399 A | 8/1985 | Flynn et al. |
| 4,678,475 A | 7/1987 | Hoshowski et al. |
| 5,102,655 A | 4/1992 | Yoshihara et al. |
| 5,384,114 A | 1/1995 | Dowell et al. |
| 5,587,155 A | 12/1996 | Ochiai et al. |
| 5,688,495 A | 11/1997 | Rosen et al. |
| 6,001,340 A | 12/1999 | Rosen et al. |
| 6,156,299 A | 12/2000 | Rosen et al. |
| 6,294,186 B1 | 9/2001 | Beerse et al. |
| 6,495,498 B2 | 12/2002 | Niemiec et al. |
| 6,858,202 B2 | 2/2005 | Niemiec et al. |
| 6,908,889 B2 | 6/2005 | Niemiec et al. |
| 7,303,744 B2 | 12/2007 | Wells |
| 7,527,654 B2 | 5/2009 | Plos |
| 8,173,144 B2 | 5/2012 | Bernard |
| 8,349,301 B2 | 1/2013 | Wells |
| 8,349,302 B2 | 1/2013 | Johnson |
| 8,361,448 B2 | 1/2013 | Johnson |
| 8,361,449 B2 | 1/2013 | Wells |
| 8,361,450 B2 | 1/2013 | Johnson |
| 8,367,048 B2 | 2/2013 | Wells |
| 8,470,305 B2 | 6/2013 | Johnson |
| 8,512,686 B2 | 8/2013 | Morioka |
| 8,968,712 B2 | 3/2015 | Tanaka |
| 9,095,528 B2 | 8/2015 | Desenne et al. |
| 9,216,146 B2 | 12/2015 | Tanaka |
| 9,259,070 B2 | 2/2016 | Fischer et al. |
| 9,265,321 B2 | 2/2016 | Fischer et al. |
| 9,271,908 B2 | 3/2016 | Allef et al. |
| 9,877,909 B2 | 1/2018 | Cetti et al. |
| 10,111,815 B2 | 10/2018 | Marsh et al. |
| 10,111,820 B2 | 10/2018 | Marsh et al. |
| 10,117,819 B2 | 11/2018 | Marsh et al. |
| 10,258,555 B2 | 4/2019 | Punyani |
| 2002/0010228 A1 | 1/2002 | Simendinger |
| 2003/0022936 A1 | 1/2003 | Milbradt et al. |
| 2003/0143173 A1 | 7/2003 | Buck |
| 2003/0170195 A1 | 9/2003 | Houze et al. |
| 2003/0199584 A1 | 10/2003 | Ahluwalia |
| 2003/0215405 A1 | 11/2003 | Parker et al. |
| 2003/0223952 A1 | 12/2003 | Wells et al. |
| 2004/0120911 A1 | 6/2004 | Shah et al. |
| 2004/0180016 A1 | 9/2004 | Buck |
| 2004/0251198 A1 | 12/2004 | Lord |
| 2005/0136015 A1 | 6/2005 | McKie et al. |
| 2005/0143268 A1 | 6/2005 | Midha et al. |
| 2005/0169869 A1 | 8/2005 | Laurent et al. |
| 2005/0175567 A1* | 8/2005 | Khoshdel .............. A61K 8/347 424/70.2 |
| 2005/0196369 A1 | 9/2005 | Ueyama et al. |
| 2005/0266034 A1 | 12/2005 | Muller et al. |
| 2006/0078523 A1 | 4/2006 | Vic |
| 2006/0165636 A1 | 7/2006 | Hasebe et al. |
| 2006/0204466 A1 | 9/2006 | Littau et al. |
| 2006/0286059 A1 | 12/2006 | Yang et al. |
| 2007/0014748 A1 | 1/2007 | Bernard |
| 2007/0104667 A1 | 5/2007 | Mondet et al. |
| 2007/0149423 A1 | 6/2007 | Warr et al. |
| 2007/0261179 A1 | 11/2007 | Dorkel et al. |
| 2008/0131389 A1 | 6/2008 | Shibuya et al. |
| 2008/0138438 A1 | 6/2008 | Taylor et al. |
| 2008/0194454 A1 | 8/2008 | Morgan et al. |
| 2009/0169502 A1 | 7/2009 | Quadir |
| 2009/0324531 A1 | 12/2009 | Okada et al. |
| 2010/0297051 A1 | 11/2010 | Feuillette |
| 2010/0300472 A1 | 12/2010 | Malle et al. |
| 2010/0330007 A1 | 12/2010 | Spindler et al. |
| 2011/0003016 A1 | 1/2011 | Burry et al. |
| 2011/0226275 A1 | 9/2011 | Fischer et al. |
| 2011/0256249 A1* | 10/2011 | Campbell .............. A61K 8/368 424/735 |
| 2011/0269658 A1 | 11/2011 | Dihora et al. |
| 2011/0274642 A1 | 11/2011 | Yamaki et al. |
| 2012/0070398 A1 | 3/2012 | Nagano et al. |
| 2012/0093751 A1 | 4/2012 | Nagano et al. |
| 2012/0308506 A1 | 12/2012 | Oku et al. |
| 2013/0064908 A1 | 3/2013 | Noh |
| 2013/0125915 A1 | 5/2013 | Nagase et al. |
| 2013/0164390 A1 | 6/2013 | Richards et al. |
| 2013/0167862 A1 | 7/2013 | Lopez et al. |
| 2013/0259817 A1 | 10/2013 | Uehara et al. |
| 2013/0259819 A1 | 10/2013 | Uehara et al. |
| 2013/0306095 A1 | 11/2013 | Syed |
| 2013/0309190 A1 | 11/2013 | Dimotakis et al. |
| 2014/0079660 A1 | 3/2014 | Doi |
| 2014/0154197 A1 | 6/2014 | Swaile et al. |
| 2014/0179645 A1 | 6/2014 | Arndt |
| 2014/0335042 A1 | 11/2014 | Peffly |
| 2015/0174052 A1 | 6/2015 | Mette et al. |
| 2015/0313816 A1 | 11/2015 | Daubresse |
| 2015/0313832 A1* | 11/2015 | Hilvert .............. A61K 8/34 132/209 |
| 2015/0359716 A1 | 12/2015 | Marsh et al. |
| 2015/0374609 A1 | 12/2015 | Cetti et al. |
| 2016/0015608 A1 | 1/2016 | Marsh et al. |
| 2016/0022558 A1 | 1/2016 | Kunin et al. |
| 2016/0158128 A1 | 6/2016 | Marsh et al. |
| 2016/0158135 A1 | 6/2016 | Marsh et al. |
| 2016/0175209 A1 | 6/2016 | Walker et al. |
| 2016/0228342 A1 | 8/2016 | Rose |
| 2016/0287494 A1 | 10/2016 | Punyani et al. |
| 2016/0287495 A1 | 10/2016 | Punyani et al. |
| 2017/0157008 A1 | 6/2017 | Punyani et al. |
| 2017/0157009 A1 | 6/2017 | Punyani et al. |
| 2017/0157011 A1 | 6/2017 | Punyani et al. |
| 2017/0216172 A1 | 8/2017 | Carballada et al. |
| 2017/0281523 A1 | 10/2017 | Punyani et al. |
| 2017/0290755 A1 | 10/2017 | Soh et al. |
| 2018/0289603 A1 | 10/2018 | Punyani et al. |
| 2018/0289605 A1 | 10/2018 | Punyani et al. |

FOREIGN PATENT DOCUMENTS

| | | |
|---|---|---|
| EP | 1787680 A2 | 5/2007 |
| EP | 1326577 B1 | 10/2008 |
| EP | 2036536 A1 | 3/2009 |
| EP | 2392314 A1 | 12/2011 |
| FR | 2931659 B1 | 3/2011 |
| FR | 2968946 B1 | 4/2013 |
| GB | 816750 | 7/1959 |
| JP | S63156711 A | 6/1988 |
| JP | H06256137 A | 9/1994 |
| JP | 3009959 B2 | 2/2000 |
| JP | 3026213 B2 | 3/2000 |

(56) References Cited

FOREIGN PATENT DOCUMENTS

| | | |
|---|---|---|
| JP | 2001122737 A | 5/2001 |
| JP | 2005145883 A | 6/2005 |
| JP | 2005194261 A | 7/2005 |
| JP | 3843051 B2 | 11/2006 |
| JP | 2006298916 A | 11/2006 |
| JP | 2007070469 A | 3/2007 |
| JP | 4329097 B2 | 9/2009 |
| JP | 4452523 B2 | 4/2010 |
| JP | 4625357 B2 | 2/2011 |
| JP | 4679893 B2 | 5/2011 |
| JP | 4883261 B2 | 2/2012 |
| JP | 5086539 B2 | 11/2012 |
| JP | 5280873 B2 | 5/2013 |
| JP | 5228338 B2 | 7/2013 |
| JP | 2014097931 A | 5/2014 |
| JP | 5779399 B2 | 9/2015 |
| WO | WO200128338 A2 | 4/2001 |
| WO | WO200128339 A2 | 4/2001 |
| WO | WO2011074134 A1 | 6/2011 |
| WO | WO2012131848 A1 | 10/2012 |
| WO | WO2014002668 A2 | 1/2014 |
| WO | WO2014100970 A1 | 7/2014 |
| WO | WO2015200778 A1 | 12/2015 |

OTHER PUBLICATIONS

"Infusion 23 (Colour) Ologie Leave-In Treatment", Procter & Gamble, Feb. 1, 2007, Mintel.
All Final and Non-Final Office Actions for U.S. Appl. No. 14/677,578.
All Final and Non-Final Office Actions for U.S. Appl. No. 14/677,636.
All Final and Non-Final Office Actions for U.S. Appl. No. 14/742,136.
All Final and Non-Final Office Actions for U.S. Appl. No. 14/742,145.
All Final and Non-Final Office Actions for U.S. Appl. No. 14/755,567.
All Final and Non-Final Office Actions for U.S. Appl. No. 14/959,234.
All Final and Non-Final Office Actions for U.S. Appl. No. 14/959,243.
All Final and Non-Final Office Actions for U.S. Appl. No. 15/093,075.
All Final and Non-Final Office Actions for U.S. Appl. No. 15/367,356.
All Final and Non-Final Office Actions for U.S. Appl. No. 15/367,369.
All Final and Non-Final Office Actions for U.S. Appl. No. 15/949,539.
All Final and Non-Final Office Actions for U.S. Appl. No. 15/949,555.
Anonymous: "Spotlight on Apricot Oil, Black Girl with Long Hair", Apr. 5, 2013, Retrieved from the internet: URL: http://blackgirllonghair.com/2013/04/spotlight-on-apricot-oil/, Retrieved Jun. 2, 2016.
John Frieda Frizzease conditioner product (John Frieda, Frizzease smooth start conditioner—https://www.johnfrieda.com/en-UK/products/frizz-ease/smooth-start-conditioner.html, last visit date: Jan. 17, 2018 (year 2018).
Khan, H., "5 ways to straighten your hair without heat", Hair Beauty Tips, Jul. 12, 2013, pp. 1-4.
Medline Plus "Aging changes in hair and nails", US National Library of Medicine, Oct. 27, 2014, pp. 1-3.
PCT International Search Report and Written Opinion for PCT/US2015/036192 dated Mar. 21, 2016.
PCT International Search Report and Written Opinion for PCT/US2015/036195 dated Dec. 16, 2015.
PCT International Search Report and Written Opinion for PCT/US2016/025827 dated Jun. 24, 2016.
PCT International Search Report and Written Opinion for PCT/US2016/064604 dated Apr. 10, 2017.
PCT International Search Report and Written Opinion for PCT/US2016/064606 dated Apr. 12, 2017.
PCT Invitation to Pay Additional Fees and, Where Applicable, Protest Fee for PCT/US2015/036192 dated Jan. 4, 2016.
PCT Invitation to Pay Additional Fees and, Where Applicable, Protest Fee for PCT/US2015/036195, dated Oct. 7, 2015.
PCT Invitation to Pay Additional Fees and, Where Applicable, Protest Fee for PCT/US2015/063888 dated Mar. 9, 2016.
PCT Invitation to Pay Additional Fees and, Where Applicable, Protest Fee for PCT/US2015/063893, dated Feb. 8, 2016.
PCT Invitation to Pay Additional Fees and, Where Applicable, Protest Fee for PCT/US2015/064608 dated Feb. 20, 2017, 9 pages.
PCT Invitation to Pay Additional Fees and, Where Applicable, Protest Fee for PCT/US2016/064604 dated Feb. 15, 2017, 10 pages.
PCT Invitation to Pay Additional Fees and, Where Applicable, Protest Fee for PCT/US2016/064606 dated Feb. 20, 2017, 14 pages.
Retrieved from internet: http://cosmetics.specialchem.com/inci/hydroxyethyl-urea, last visit May 10, 2017.
U.S. Appl. No. 15/949,539, filed Apr. 10, 2018, Punyani.
U.S. Appl. No. 15/949,555, filed Apr. 10, 2018, Punyani.
All final and non-final office actions for U.S. Appl. No. 15/473,832.
Dow Corning: "Get on the FastTrack to Dry with silicones from Dow Corning", Nov. 19, 2015.
Dow Corning: "Leave-In Conditioner: Fast Dry", Dec. 9, 2015.
Dow Corning: "Revivel Hair Repair Cream: Ideal to Repair Heat Damaged Hair", Jan. 21, 2015.
Dow Corning: "Rinse-Off Conditioner: Fast Dry", Dec. 9, 2015.
Knothe et al., J. Am Oil Chem Soc., 86, pp. 843-856 (2009).
Merriam-Webster Dictionary, obtained online at https://www.merriam-webster.com/dictionary/pH, downloaded on Jun. 29, 2018, pp. 1-14 (2018).
Naturally.com, "Salicylic Acid Shampoo for Curly Hair", pp. 1-3, 2011.
PCT International Search Report and Written Opinion for PCT/US2017/024965 dated Jun. 13, 2017.
Watson, "5 Hair Conditioners You Can Make At Home", retrieved from on-line website: www.wisebread.com, pp. 1-11, 2011.
Benvenuti, http://www.futurederm.com/what-is-the-best-oil-for-your-hair-argan-oil-vs-pequi-oil-review/, 2011, downloaded Dec. 30, 2018.
LotionCrafter (https://lotioncrafter.com/reference/tech_data_lc995.pdf) available on archieve.org on Nov. 23, 2015, pp. 1-2 (2015).
Olivella, M., et al., "Salicylic acid permeation: A comparative study with different vehicles and membranes", Biocell, pp. 321-324Year: 2006).

\* cited by examiner

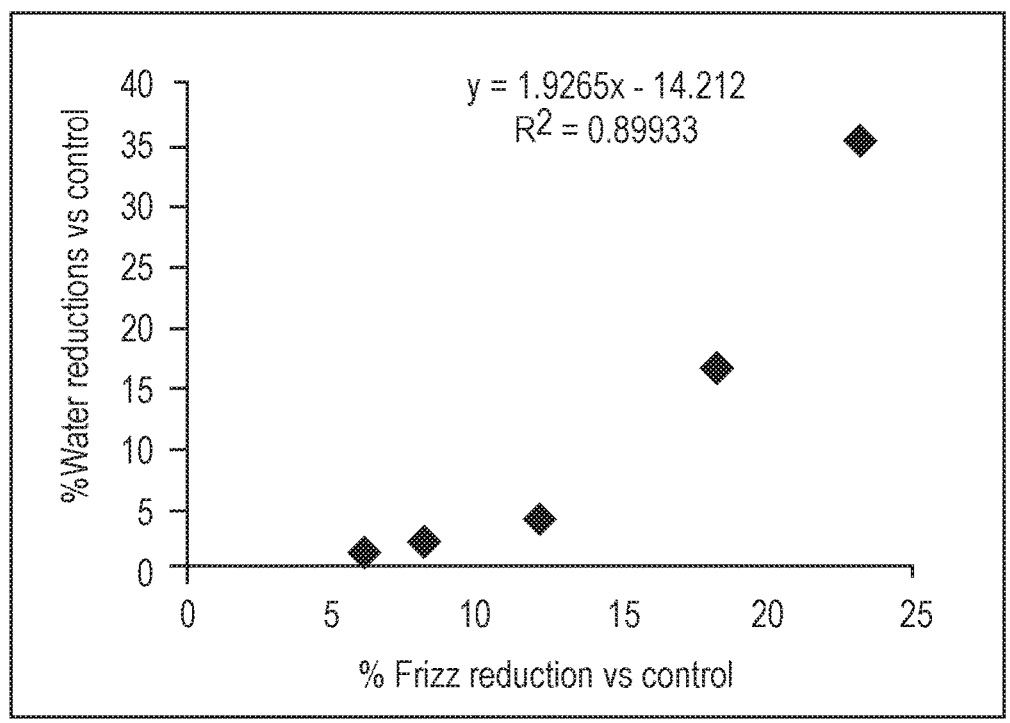

HAIR CARE REGIMEN USING COMPOSITIONS COMPRISING MOISTURE CONTROL MATERIALS

FIELD OF THE INVENTION

Described herein is a method of reducing hair frizz by treating hair with a regimen comprising two or more hair care compositions wherein at least two of such compositions comprise Moisture Control Materials.

BACKGROUND OF THE INVENTION

Hair frizz is described by consumers as the appearance of unruly fibers at the top of the scalp and tips of hair as well as an increased volume through the bulk of the hair. Generally they see this frizz on days when there is humid weather and the level of moisture in the air is high. The appearance of frizz is undesired and it is often associated with a loss of shine and smoothness. The appearance of frizz and loss of shine and smoothness are associated with a perception of poor hair health. The basic mechanism causing frizz in high humid environments is that at high humidity water penetrates into hair and changes the chemical bond interactions inside the hair. During styling, the consumer will create a 'wet set' where hair is blow dried or flat ironed to create the desired shape. During drying, water is evaporated from hair and hydrogen bonds are formed between the protein peptide chains holding the style in place. As moisture diffuses into hair the hydrogen bonds are broken and hair returns back to its natural shape. For consumers who straighten their hair by blow drying or flat ironing this return to a curled style is associated with a loss of alignment and increased volume. In addition, at high moisture levels in hair the fiber diameter increases which also increases the overall volume of hair.

The typical strategy to prevent frizz is to formulate leave-on and other hair care products with surface-depositing materials such as silicone, oils, conditioning silicone etc. which make hair more hydrophobic and decrease inter-fiber interactions. At high levels these materials can also provide increased cohesive forces holding fibers together to prevent frizz from occurring. With these materials depositing on the hair surface a greasy look and feel is typically experienced, which is an undesired trade-off of frizz reduction.

Consequently, a need exists for treatments that combine effective frizz control with additional hair benefits that the consumer can notice and feel and, at the same time, is delightful to use without having a sticky or greasy feel.

SUMMARY OF THE INVENTION

The present invention is directed to a method for hair frizz reduction comprising the steps of:
a) performing a hair cleansing by applying to the hair a shampoo composition and rinsing the shampoo composition from the hair with water;
b) performing one or more additional hair treatment steps selected from the group containing:
  (1) a rinse-off conditioner treatment using a rinse-off conditioner composition;
  (2) a soaking treatment using a soaking treatment composition;
  (3) a deep conditioner treatment using a deep conditioner treatment composition; and
  (4) a leave-on treatment using a leave-on treatment composition;
wherein step (a) is performed before (b),
and wherein the leave-on treatment, if present in the method, is performed as the last step after all the other treatments,
and further wherein at least two of the compositions used in steps (a) and (b) comprise from about 0.1 to about 20% of one or more moisture control material selected from the group containing:
i. Class I Moisture Control Material having the structure selected from:

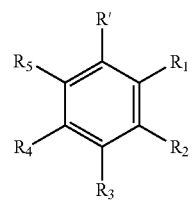

wherein R' is —COOY, sulfonic acid, or —C=CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH=CH—COOR, and wherein the moisture control material is an acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0;

ii. Class IIa having the structure selected from:

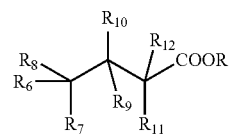

wherein R is hydrogen or metal ion, $R_6$ is methyl, ethyl, propyl, alkenyl or phenyl having less than 12 carbon atoms and wherein $R_7$, $R_8$, $R_9$, $R_{10}$, $R_{11}$, $R_{12}$ are hydrogen, methyl, ethyl, propyl, phenyl, hydroxyl, methoxy or ethoxy groups;

iii. Class IIb having the structure selected from:

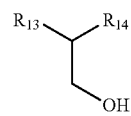

an alcohol wherein R13 is an alkyl, alkenyl, straight or branched carbon chains and; and wherein R14 is hydrogen, hydroxyl, alkyl, methyl, ethyl and propyl wherein the structure of such alcohol contains less than 20 total carbon atoms;

iv. Class IIc being an alcohol comprising an unsaturated double bond in the C2 position;

v. Class IId being an alkyl-substituted glycol wherein the structure of such alkyl substituted glycol contains less than 20 carbon atoms;

vi. Class IIe being a monoalkyl or dialkyl substituted glycerin or mono- or di-esters of glycerin with fatty acids wherein the structure of such monoalkyl- or dialkyl-substituted glycerin or glycerin esters contains less than 20 total carbon atoms;

vii. Class IIf having a structure the structure selected from:

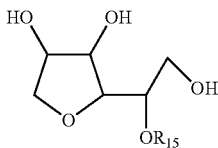

wherein $R_{15}$ could be hydrogen, alkyl, alkenyl, phenyl group and wherein the structure of the $R_{13}$ group contains less than 20 carbon atoms;

viii. Class IIg being a fatty acid ester containing from 15-40 total carbon atoms; and wherein the moisture control material of Class II is weakly to non-acidic and further wherein the moisture control material of Class II has protein binding higher than 10 and molecular volume lower than 1500 and log P higher than 0.5 and pKa of 5 or higher and hydrogen-binding higher than 4;

and further wherein hair treated with the method for hair frizz reduction absorbs moisture at least 2% less than hair treated with the corresponding combination of treatments having no moisture control material, wherein the moisture absorption is measured using DVS method.

Without being bound by theory, the method for hair frizz reduction of the present invention provide excellent frizz performance without a negatively affecting hair feel. The Moisture Control Material that are contained in at least two of the compositions of the regimen prevent water uptake into hair under high humidity conditions, reducing the negative impact of frizz. By providing frizz benefits by penetrating the hair fiber as opposed to depositing on the hair surface, the frizz benefit is not associated by negative hair feel, which is typically observed with current commercial anti-frizz products and treating methods. These and additional features provided by the embodiments of the present invention will be more fully understood in view of the following detailed description. Method of treating air comprising two or more steps using two or more hair compositions containing moisture control materials has higher benefit in one time application to hair than using one hair composition such as leave on. This is because of moisture control material have accumulative effect and also method of treatment is optimized with dosage and duration of application. In case of regimen, moisture control materials penetrates approximately four times higher than leave on in one time application to hair and approximately three times higher than conventional regimen comprising of shampoo, conditioner and leave on in one time application to hair.

BRIEF DESCRIPTION OF THE DRAWINGS

FIG. 1 is graph depicting that there is a monotonic correlation between % water reduction and % frizz reduction.

DETAILED DESCRIPTION OF EMBODIMENTS OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity (RH), unless otherwise designated. All numeric ranges are inclusive of narrower ranges; delineated upper and lower range limits are combinable to create further ranges not explicitly delineated.

The compositions used in the method of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application" as used in reference to a composition, means to apply or spread the compositions of the present invention onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

"Regimen," in reference to the present invention, means a method of treating hair comprising two or more steps using two or more hair care compositions, wherein the steps are performed in the shower or out of the shower. Optionally, these steps may be followed by air-drying, blow drying, hot steam, hot iron or a combination of these without any intermediate rinsing or washing. Method of treating air comprising two or more steps using two or more hair compositions containing moisture control materials has higher benefit in one time application to hair than using one hair composition such as leave on. This is because of moisture control material have accumulative effect and also method of treatment is optimized with dosage and duration of application. In case of regimen, moisture control materials penetrates approximately 4 times higher than leave on in one time application to hair and approximately 3 times higher than conventional regimen comprising of shampoo, conditioner and leave on in one time application to hair.

"Rinse-off conditioner" treatment in the present invention is defined as a hair treatment using a rinse-off conditioner composition, wherein (a) the rinse-off conditioner composition is applied onto hair, and (b) wherein the rinse-off conditioner composition is allowed to remain on the consumer's hair for less than 3 minutes before rinsing the rinse-off the conditioner composition from the hair with water.

"Leave-on treatment" in the present invention is defined as a hair treatment using a leave-on treatment composition, wherein the leave-on treatment composition is applied onto hair and wherein the leave-on treatment composition is not rinsed from the hair. The leave-on compositions may be substantially free of cleansing or detersive surfactants. For example, "leave-on compositions" may be left on the keratinous tissue for at least 15 minutes. For example, leave-on compositions may comprise less than 1% detersive surfactants, less than 0.5% detersive surfactants, or 0% detersive surfactants. The compositions may, however, contain emulsifying, dispersing or other processing surfactants that are not intended to provide any significant cleansing benefits when applied topically to the hair.

"Deep Conditioner Treatment" in the present invention is defined as a hair treatment using a deep conditioner treatment composition, wherein (a) an amount equal to or higher than 0.2 g of the deep conditioner treatment composition is applied onto hair per gram of hair, and (b) wherein the composition is allowed to remain on the consumer's hair for at least 3 minutes before rinsing with water or washing, or wiping. The deep conditioner treatment may be followed by air-drying, blow drying, hot steam, hot iron or a combination thereof.

"Soaking treatment" in the present invention is defined as a hair treatment using a soaking treatment composition wherein the consumer's hair is partially or completely immersed into the composition. Soaking hair treatments are to be distinguished from typical hair leave-on and rinse-off treatments, which use products that are applied onto the hair and/or scalp by dispensing the product (a) directly onto the hair and/or scalp or (b) on the consumer hand or hands and then applying onto the hair or scalp. Application of the product for typical leave-on and rinse-off treatments is performed by spraying or spreading, In soaking treatments, the step of immersion of hair into soaking compositions may be followed by a washing step with shampoo (or not). The soaking step may be also followed by rinsing, wiping, or the like. Alternatively, the soaking step may be followed by hot steam, air-drying, blow drying, hot iron or a combination of these without any intermediate rinsing or washing. The Soaking compositions may be substantially free of cleansing or detersive surfactants. For example, "Soaking compositions" may be left on the keratinous tissue for at least 2 minutes. For example, Soaking compositions may comprise less than 1% detersive surfactants, less than 0.5% detersive surfactants, or 0% detersive surfactants. The compositions may, however, contain emulsifying, dispersing or other processing surfactants that are not intended to provide any significant cleansing benefits when applied topically to the hair.

"Soluble" means at least about 0.1 g of solute dissolves in 100 ml of solvent, at 25° C. and 1 atm of pressure.

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. The weight average molecular weight may be measured by gel permeation chromatography. "QS" means sufficient quantity for 100%.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. Polymers made from two or more different types of monomers are called copolymers. The distribution of the different monomers can be calculated statistically or block-wise—both possibilities are suitable for the present invention. Except if stated otherwise, the term "polymer" used herein includes any type of polymer including homopolymers and copolymers.

The mechanism of action for frizz generation involves moisture from the environment being absorbed by hair and occupying hydrogen bonding sites within hair, including those on the peptide backbone and also associated with acidic and basic side chains of amino acid residues such as lysine, arginine and glutamic acid. This internal water replaces hydrogen bonds that had been created during styling that hold hair in a desired configuration. As a consequence, hair returns to its natural shape which typically leads to unwanted wave, loss of alignment and frizz. In addition, uptake of water by these hydrogen bonding sites swells the hair fiber causing style expansion, which is another indicator of fizz. Without being bound by theory, the materials covered by this invention will replace water at the hydrogen bond sites inside hair and prevent water uptake. Reduction of water inside hair will lead to a reduction in the appearance of frizz under high humidity conditions. Because the mechanism of action is related to the space inside the hair fibers, there are no feel negatives, such as, for example, greasy or oily feel associated with the benefit. The reduction in water uptake is measured using Dynamic Vapor Sorption (DVS) method, which measures a weight increase of hair equilibrated at 0% Relative Humidity (RH) versus 90% RH. Significant frizz benefit is measured on hair treated by materials that caused a reduction in water uptake of higher than 5% versus control hair that is not treated with such materials. The treatment involved the application of a 2% w/w solution of the material in 50:50 water:ethanol solvent.

Preferred materials include salicylic acid, 2,3-dihydroxybenzoic acid, 2,6-dihydroxybenzoic acid, 3-aminobenzoic acid, gallic acid, ethyl gallate, 5-chlorosalicylic acid, trans-ferulic acid, p-coumaric acid, ricinoleic acid, isovaleric acid, isobutyric acid, 2-hexyl-1-decanol, phytol and sorbitan caprylate. These materials are chosen from Molecular Class I and/or Molecular Class II or can also be used in combination to increase the size of the benefit.

In an embodiment of the present invention, the concentration of the Moisture Control Material or the concentration of the mixture of Moisture Control Material in two or more of the hair care composition of the method is from about 0.1% to about 20%, in an embodiment from about 0.1% to about 15%; in an embodiment from about 0.2% to about 8%, in a further embodiment from about 0.5% to about 5%, and in yet a further embodiment from about 1.0% to about 3.0%. Molecular Class I: Polar, Acidic Compounds with the Following Properties:

Protein Binding (PB)>20 AND Molecular Volume (Mol. Vol).<500 AND log P<3 AND Hydrogen-binding (H-binding)>10 AND pKa<5.0, wherein PB is % protein binding, Mol. Vol is molecular volume (in $Å^3$); log P is n-octanol/water partition coefficients. These properties can be calculated using Volsurf software (http://www.moldiscovery.com/soft_volsurf.php). H-bond is the energy from hydrogen bonds between molecules from Hansen Solubility Parameters and pKa value is a logarithmic measure of the acid dissociation constant.

| Name (1% wt/vol) | PB | Mol. Vol. | log P | pKa | H-bond (MPa^½) | % Water Reduction |
|---|---|---|---|---|---|---|
| 2,4-Dihydroxybenzoic acid | 28 | 324 | 1.5 | 3.2 | 23 | 30 |
| 3-Hydroxybenzoic Acid | 38 | 314 | 1.6 | 4.3 | 20 | 20 |
| Gallic acid | 23 | 337 | 0.9 | 4.4 | 23 | 15 |
| 3-Aminobenzoic acid | 41 | 326 | 0.9 | 3.6 | 16 | 12 |
| 4-Aminobenzoic acid | 42 | 323 | 0.9 | 3.5 | 16 | 12 |
| 2,5-Dihydroxybenzoic acid | 31 | 329 | 1.6 | 2.9 | 23 | 27 |
| 3,4-Dihydroxybenzoic acid | 27 | 327 | 0.9 | 4.4 | 23 | 20 |
| 3,5-Dihydroxybenzoic acid | 27 | 327 | 0.9 | 4.1 | 23 | 15 |
| 2,6-Dihydroxybenzoic acid | 37 | 326 | 1.6 | 2.1 | 23 | 35 |
| 5-Chlorosalicylic acid | 56 | 361 | 2.3 | 3.0 | 21 | 28 |
| Salicylic acid | 44 | 320 | 2.1 | 3.1 | 20 | 18 |
| Trans-Ferulic Acid | 50 | 451 | 1.5 | 4.5 | 19 | 6 |
| p-Coumaric acid | 46 | 391 | 1.6 | 4.5 | 20 | 8.8 |
| 4-Hydroxybenzenesulphonic acid | 55 | 271 | 1.5 | 2.7 | 22 | 26 |
| 3-Chloro-4-hydroxybenzoic acid | 49 | 356 | 2.1 | 4.1 | 20 | 11 |
| 3,5-Dichloro-4-hydroxybenzoic acid | 51 | 397 | 2.8 | 3.8 | 20 | 15 |
| 2,5 Dihydroxyterephthalic acid | 20 | 375 | 1.1 | 2.1 | 22 | 18 |
| 3-Aminophenol | 45 | 284 | 0.6 | 4 | 17 | 14 |
| 3-Hydroxyanilinium chloride | 32 | 280 | 0.6 | 4 | 17 | 16 |
| 2-Aminophenol | 49 | 288 | 1.0 | 4 | 17 | 14 |
| 4-Aminophenol | 39 | 284 | 0.6 | 4 | 17 | 10 |
| N-4-Hydroxyphenylglycine | 37 | 388 | 1.3 | 3 | 13 | 15 | b) Molecular Class II: Weakly polar to non-polar, weakly to non-acidic compounds that have the following properties: PB>10 AND Mol. Vol.<1500 AND log P>0.5 AND pKa≥5 AND H-binding>4, wherein PB is % protein binding, Mol. Vol is molecular volume (in $Å^3$); log P is n-octanol/water partition coefficients. These properties can be calculated using Volsurf software (http://www-.moldiscovery.com/soft_volsurf.php). H-bond is the energy from hydrogen bonds between molecules from Hansen Solubility Parameters and pKa value is a logarithmic measure of the acid dissociation constant.

| Name | PB | Mol. Vol. | logP | pKa | H-bond (MPa^½) | % water reduction |
|---|---|---|---|---|---|---|
| 2-Hydroxyethyl salicylate | 45 | 419 | 1.5 | 8.3 | 19.1 | 10 |
| Ethyl Gallate | 43 | 431 | 1.4 | 8.7 | 22.6 | 17 |
| Oleic Acid | 100 | 832 | 7 | 5 | 6.4 | 14 |
| Ricinoleic acid | 84 | 841 | 5.9 | 5 | 17.8 | 8.8 |
| Isovaleric acid | 29 | 295 | 1.3 | 5 | 9.7 | 15 |
| Isobutyric acid | 15 | 254 | 1 | 5 | 10.4 | 5 |
| 2-Hexyl-1-decanol | 87 | 745 | 6.8 | 15 | 10.1 | 11 |
| Phytol | 100 | 874 | 8.0 | 13 | 9.6 | 14 |
| Sorbitan Caprylate | 32 | 695 | 1.3 | 12 | 21.8 | 11 |
| Glyceryl monooleate | 96 | 974 | 6.27 | 12.8 | 16.2 | 5 |
| Isostearyl isostearate | 100 | 1527 | 14.7 | 14 | 4.2 | 11 |
| Ethyl linoleate | 82 | 903 | 7.71 | 7.8 | 5.1 | 8 |
| Isopropyl myristate | 97 | 798 | 6.99 | 8.8 | 5.0 | 12 |
| Octyl Salicylate | 82 | 646 | 5.4 | 7.1 | 11.7 | 14 |

A Class I having the structure selected from:
1) Class I having the structure selected from:

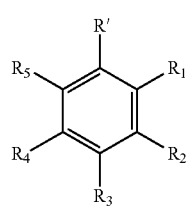

wherein R' is —COOY, sulfonic acid, or —C═CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH═CH—COOR, and wherein the moisture control material is an acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0;

2) Class II having the structure selected from:
A)

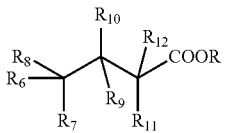

wherein R is hydrogen or metal ion, $R_6$ is methyl, ethyl, propyl, alkenyl or phenyl having less than 12 carbon atoms and wherein $R_7$, $R_8$, $R_9$, $R_{10}$, $R_{11}$, $R_{12}$ are hydrogen, methyl, ethyl, propyl, phenyl, hydroxyl, methoxy or ethoxy groups;
B)

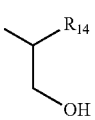

an alcohol wherein R13 is an alkyl, alkenyl, straight or branched carbon chains and; and wherein R14 is hydrogen, hydroxyl, alkyl, methyl, ethyl and propyl wherein the structure of such alcohol contains less than 20 total carbon atoms;
c) An alcohol comprising an unsaturated double bond in the C2 position. A non limiting example would be phytol.
d) an alkyl-substituted glycol wherein the structure of such alkyl substituted glycol contains less than 20 carbon atoms;
e) a monoalkyl or dialkyl substituted glycerin or mono- or di-esters of glycerin with fatty acids wherein the structure of such monoalkyl- or dialkyl-substituted glycerin or glycerin esters contains less than 20 total carbon atoms;

f)

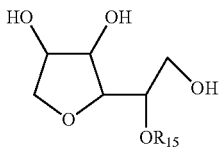

wherein $R_{15}$ could be hydrogen, alkyl, alkenyl, phenyl group and wherein the structure of the $R_{13}$ group contains less than 20 carbon atoms;

g) a fatty acid ester containing from 15-40 total carbon atoms and wherein the moisture control material of Class II is weakly to non-acidic and further wherein the moisture control material of Class II has protein binding higher than 10 and molecular volume lower than 1500 and log P higher than 0.5 and pKa of 5 or higher and hydrogen-binding higher than 4;

pH of Compositions

Below is the data of the difference of % water reduction of hair treated with leave on composition containing 1% salicylic acid in ethanol:water (50:50) at various values of pH vs control (hair treated with composition of ethanol:water (50:50). As shown in below table, at lower pH, the present invention demonstrates improved performance compared to higher pH.

| Raw Material | Formula Example | | | |
| --- | --- | --- | --- | --- |
| | pH 3 | pH 4.2 | pH 7 | pH 10 |
| Distilled Water | QS | QS | QS | QS |
| Ethanol | 50.0 | 50.0 | 50.0 | 50.0 |
| Salicylic acid | 1.0 | 1.0 | 1.0 | 1.0 |
| Final pH | 3.2 | 4.2 | 7 | 10 |
| % Water Reduction | 30 | 27 | 22 | 15 |

In an embodiment of the present invention, the pH of a composition of the present invention comprising material from Molecular Class I may be in the range of from about 1 to about 9, in another embodiment a pH of from about 2 to about 7, in a further embodiment a pH of from about 4 to about 5.5.

In an embodiment of the present invention, the Moisture control Material is a carboxylic acid ester. In an embodiment, the carboxylic acid ester is based on a fatty acid wherein the molecule of the fatty acid comprises of more than 14 carbon atoms. Non-limiting examples of such esters are isostearyl isostearate, methyl stearate, methyl palmitate, and methyl oleate. In another embodiment of the present invention, the carboxylic acid ester is part of a mixture of materials prepared via the reaction of natural oils using methanol. Non-limiting examples of such mixture is the mixture that is produced by the product of the reaction of refined palm kernel oil with methanol, followed by fractionation via distillation. A commercial product that meets this description is the Heavy Cut Ester CE-1875 (supplied by P&G Chemicals with CAS Number 6772-38-3) containing ingredients such as methyl stearate, methyl palmitate, methyl oleate as major ingredients, as well as methyl laurate, methyl myristate, methyl behenate and other materials as minor ingredients.

The various compositions of the method for hair frizz reduction of the present invention and some of their ingredients are described below.

Shampoo Composition

The method of reducing fizz described herein comprises applying to the hair a shampoo composition. The shampoo composition delivers consumer desired cleansing and potentially conditioning. It can also deliver frizz reduction in the case that it contains a moisture control material. The shampoo composition may comprise from about 0.1% to about 15% moisture control material selected from the group consisting Class I and Class II materials. After applying to the hair a shampoo composition as described herein, the method then comprises rinsing the shampoo composition from the hair.

A. Detersive Surfactant

The shampoo composition comprises one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

Suitable amphoteric or zwitterionic surfactants for use in the shampoo composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The shampoo composition may also comprise a shampoo gel matrix, an aqueous carrier, and other additional ingredients described herein.

B. Aqueous Carrier

The shampoo composition comprises a first aqueous carrier. Accordingly, the formulations of the shampoo composition can be in the form of pourable liquids (under ambient conditions). Such compositions will therefore typically comprise a first aqueous carrier, which is present at a level of at least 20 wt %, from about 20 wt % to about 95 wt %, or from about 60 wt % to about 85 wt %. The first aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The first aqueous carriers useful in the shampoo composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

C. Shampoo Gel Matrix

The shampoo composition described herein may comprise a shampoo gel matrix. The shampoo gel matrix comprises (i) from about 0.1% to about 20% of one or more fatty alcohols, alternative from about 0.5% to about 14%, alternatively from about 1% to about 10%, alternatively from about 6% to about 8%, by weight of the shampoo gel matrix; (ii) from about 0.1% to about 10% of one or more shampoo gel matrix surfactants, by weight of the shampoo gel matrix; and (iii) from about 20% to about 95% of an aqueous carrier, alternatively from about 60% to about 85% by weight of the shampoo gel matrix.

The fatty alcohols useful herein are those having from about 10 to about 40 carbon atoms, from about 12 to about 22 carbon atoms, from about 16 to about 22 carbon atoms, or about 16 to about 18 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof. Mixtures of cetyl and stearyl alcohol in a ratio of from about 20:80 to about 80:20 are suitable.

The shampoo gel matrix surfactants may be any of the detersive surfactants described in section "A" herein.

The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier useful herein includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Rinse Off Conditioner Composition or Deep Conditioner Treatment Composition

The method of reducing frizz described herein may comprise applying to the hair a rinse-off conditioner composition and/or a deep conditioner treatment composition. The rinse-off conditioner composition and the deep conditioner treatment composition delivers consumer desired hair conditioning. It can also deliver frizz reduction in the case that it contains a moisture control material. The rinse-off conditioner composition and the deep conditioner treatment composition may comprise from about 0.1% to about 15% moisture control material selected from the group consisting Class I and Class II materials. After applying to the hair a rinse-off conditioner composition as described herein, the method then comprises rinsing the conditioner composition from the hair. This is also true for the deep conditioner treatment composition The rinse-off conditioner composition and the deep conditioner treatment composition may also comprise a conditioner gel matrix comprising (1) one or more high melting point fatty compounds, (2) a cationic surfactant system, and (3) an aqueous carrier.

High Melting Point Fatty Compound

The high melting point fatty compound can be included in the composition at a level of from about 0.5%, preferably from about 1.0%, more preferably form about 1.5%, still more preferably from about 2%, even more preferably from about 4%, and to about 15%, preferably to about 10% by weight of the composition, in view of providing the benefits of the present invention. The high melting point fatty compound useful herein have a melting point of 25° C. or higher, preferably 40° C. or higher, more preferably 45° C. or higher, still more preferably 50° C. or higher. In the present invention, the high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature.

Among a variety of high melting point fatty compounds, fatty alcohols are suitable for use in the conditioner composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

Cationic Surfactant System

The gel matrix of the rinse-off and the deep conditioner composition includes a cationic surfactant system. The cationic surfactant system can be one cationic surfactant or a mixture of two or more cationic surfactants. Preferably, the cationic surfactant is selected from mono-long alkyl quaternized ammonium salt, di-long alkyl quaternized ammonium salt, mono-long alkyl amidoamine salt or mixtures thereof. The cationic surfactant system can be included in the composition at a level by weight of from about 0.1% to about 10%, from about 0.5% to about 8%, from about 0.8% to about 5%, and from about 1.0% to about 4%.

The mono-long alkyl quaternized ammonium salt cationic surfactants useful herein are those having one long alkyl chain which has from about 12 to about 30 carbon atoms, preferably from 16 to 24 carbon atoms, more preferably 18 to 22 carbon atoms. The remaining groups attached to the nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms. The counterion is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Nonlimiting examples of such mono-long alkyl quaternized ammonium salt cationic surfactants include: behenyl trimethyl ammonium salt.

The di-long alkyl quaternized ammonium salt cationic surfactants useful herein are those having two long alkyl chains of from 12 to 30 carbon atoms, more preferably from 16 to 24 carbon atoms, still more preferably from 16 to 22 carbon atoms or an aromatic, alkoxy, polyoxyalkylene, alkylamido, hydroxyalkyl, aryl or alkylaryl group having up to about 30 carbon atoms. The remaining substituents on the nitrogen atom are selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms. The counterion is a salt forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Nonlimiting examples of di-long alkyl cationic surfactants include: dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide.

Aqueous Carrier

The conditioner gel matrix of the conditioner composition (and the deep conditioner treatment composition) includes an aqueous carrier. Accordingly, the formulations of the conditioner composition can be in the form of pourable liquids (under ambient conditions). Such compositions will therefore typically comprise an aqueous carrier, which is present at a level of from about 20 wt % to about 95 wt %, or from about 60 wt % to about 85 wt %. The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carriers useful in the conditioner composition (and the deep conditioner treatment composition) include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Soaking Treatment Composition

The method of reducing frizz described herein may comprise the use of a soaking treatment composition. The soaking treatment composition delivers frizz reduction in the case that it contains a moisture control material; it can also deliver consumer desired hair conditioning benefit. The soaking treatment composition may comprise from about 0.1% to about 15% moisture control material selected from the group consisting Class I and Class II materials. After inserting the consumer hair (partially or completely) into the soaking treatment composition, the soaking treatment may be followed by a washing step with shampoo (or not). The soaking step may be also followed by rinsing, wiping, or the like. Alternatively, the soaking step may be followed by hot steam, air-drying, blow drying, hot iron or a combination of these without any intermediate rinsing or washing. The Soaking compositions may be substantially free of cleansing or detersive surfactants. For example, "Soaking compositions" may be left on the keratinous tissue for at least 2 minutes. For example, Soaking compositions may comprise less than 1% detersive surfactants, less than 0.5% detersive surfactants, or 0% detersive surfactants. The compositions may, however, contain emulsifying, dispersing or other processing surfactants that are not intended to provide any significant cleansing benefits when applied topically to the hair.

Viscosity of the Soaking Treatment Composition

The compositions have viscosities of from about 100 cps to about 1000 mPa*s at 1 s−1, as measured at 25.0 deg. C. using an AR2000 viscometer (TA Instruments of New Castle, Del.) using an acrylic 60 mm, 2 deg. flat cone. Viscosity can also be determined by other conventional methods readily known in the art.

The product viscosity (measured via Brookfield rotational viscometer) is less than about 1000 cP, in a further embodiment less than about 500 cP, and in another embodiment in the range of about 100-1000 cP.

The viscosity herein is measured on a Brookfield viscometer model #LVDVII+ at 20 deg. C. The spindle used for these measurements is a S31 spindle with the appropriate speed to measure products of different viscosities; e.g., 12 rpm to measure products of viscosity greater than 1000 cP; 30 rpm to measure products with viscosities between 500-1000 cP; 60 rpm to measure products with viscosities less than 500 cP.

Carrier

According to another aspect of the present invention, the soaking treatment compositions may include at least about 20 weight percent of an aqueous carrier. According to one embodiment, the aqueous carrier may be prepared from demineralized or distilled water, for example. In an embodiment of the present invention, the carrier may comprise water, organic solvents (miscible or non-miscible with water), silicone solvents or a mixture thereof. In one embodiment of the present invention, a volatile carrier may include water or a mixture of water and organic solvents. In a further embodiment, the solvents may be dermatologically acceptable. In a further embodiment, the carrier may comprise water with minimal or no significant concentrations of organic solvent, except as otherwise incidentally incorporated into the composition as minor ingredients of other components. In another embodiment, water, organic and silicone solvents that have boiling points below or equal to 250° C. may be volatile solvents and volatile carriers. In one embodiment, solvents with boiling points above 250° C. may be considered non-volatile.

Non-limiting examples of a carrier may include water and solutions or mixtures of water with lower alkyl alcohols and/or polyhydric alcohols. Examples of lower alkyl alcohols are monohydric alcohols having 1 to 6 carbons such as ethanol, methanol, propanol, isopropanol, butanol, pentanol, and hexanol. Examples of polyhydric alcohols are glycols, such as dipropylene glycol, propylene glycol, butylene glycol, 1,4-butanediol, 3-allyloxy-1,2-propanediol, 1,2-hexanediol, 1,6-hexanediol, 1,3-butanediol, 1,3-propanediol, 2,2'-thiodiethanol, glycerin and other diols.

Other non-limiting examples of solvent include ethers, such as dipropylene glycol n-butyl ether, sugars, and sugar derivatives.

Leave-on Treatment

The method of reducing frizz described herein may comprise applying to the hair a leave-on treatment composition. The leave-on treatment described herein may deliver consumer desired conditioning. It can also deliver frizz reduction in the case that it contains a moisture control material. The leave-on conditioner composition may comprise from about 0.1% to about 15% moisture control material selected from the group consisting Class I and Class II materials. The conditioner composition may also comprise:
 (a) a conditioner gel matrix comprising (1) one or more high melting point fatty compounds, (2) a cationic surfactant system, and (3) an aqueous carrier; and/or
 (b) one or more rheology modifiers; and
 (c) an aqueous carrier.

Aqueous Carrier

The formulations of the leave-on treatment can be in the form of pourable liquids (under ambient conditions). Such compositions will therefore typically comprise an aqueous carrier, which is present at a level of at least 20 wt %, from about 20 wt % to about 95 wt %, or from about 60 wt % to about 85 wt %. The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carriers useful in the leave-on treatment include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Additional Components

The hair care compositions such as shampoo composition, rinse-off conditioner composition, the deep conditioner composition, the soaking composition and the leave-on treatments described herein may optionally comprise one or more additional components known for use in hair care or personal care products, provided that the additional components are physically and chemically compatible with the essential components described herein, or do not otherwise unduly impair product stability, aesthetics or performance. Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the hair care compositions.

Non-limiting examples of additional components for use in the hair care compositions include conditioning agents, natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

1. Conditioning Agent

The hair care compositions may comprise one or more conditioning agents. Conditioning agents include materials that are used to give a particular conditioning benefit to hair. The conditioning agents useful in the hair care compositions of the present invention typically comprise a water-insoluble, water-dispersible, non-volatile, liquid that forms emulsified, liquid particles. Suitable conditioning agents for use in the hair care composition are those conditioning agents characterized generally as silicones, organic conditioning oils or combinations thereof, or those conditioning agents which otherwise form liquid, dispersed particles in the aqueous surfactant matrix.

One or more conditioning agents are present from about 0.01 wt % to about 10 wt %, from about 0.1 wt % to about 8 wt %, and from about 0.2 wt % to about 4 wt %, by weight of the composition.

Silicone Conditioning Agent

The compositions of the present invention may contain one or more silicone conditioning agents. Examples of the silicones include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, sugar or polysaccharide groups, fluorine-modified alkyl groups, alkoxy groups, or combinations of such groups. Such silicones may be soluble or insoluble in the aqueous (or non-aqueous) product carrier. In the case of insoluble liquid silicones, the polymer can be in an emulsified form with droplet size of about 10 nm to about 30 micrometers Organic Conditioning Materials The conditioning agent of the compositions of the present invention may also comprise at least one organic conditioning material such as oil or wax, either alone or in combination with other conditioning agents, such as the silicones described above. The organic material can be nonpolymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-20 200, PEG-400, PEG-600, PEG-1000, PEG-2M, PEG-7M, PEG-14M, PEG-45M and mixtures thereof.

2. Rheology Modifier

In one embodiment the hair care product may include one or more rheology modifiers to adjust the rheological characteristics of the composition for better feel, in-use properties and the suspending stability of the composition. For example, the rheological properties are adjusted so that the composition remains uniform during its storage and transportation and it does not drip undesirably onto other areas of the body, clothing or home furnishings during its use. Any suitable rheology modifier can be used. In an embodiment, the leave-on treatment may comprise from about 0.01% to about 3% of a rheology modifier, alternatively from about 0.1% to about 1% of a rheology modifier, The one or more rheology modifier may be selected from the group consisting of polyacrylamide thickeners, cationically modified polysaccharides, associative thickeners, and mixtures thereof. Associative thickeners include a variety of material classes such as, for example: hydrophobically modified cellulose derivatives; hydrophobically modified alkoxylated urethane polymers, such as PEG-150/decyl alcohol/SMDI copolymer, PEG-150/stearyl alcohol/SMDI copolymer, polyurethane-39; hydrophobically modified, alkali swellable emulsions, such as hydrophobically modified polypolyacrylates, hydrophobically modified polyacrylic acids, and hydrophobically modified polyacrylamides; hydrophobically modified polyethers. These materials may have a hydrophobe that can be selected from cetyl, stearyl, oleayl, and combinations thereof, and a hydrophilic portion of repeating ethylene oxide groups with repeat units from 10-300, alternatively from 30-200, and alternatively from 40-150. Examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

Non-limiting examples of additional rheology modifiers include acrylamide/ammonium acrylate copolymer (and) polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (MEHEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol 1342, Sepigel™ 305, Simulgel™600, Sepimax Zen, and/or combinations thereof.

3. Benefit Agents

In an embodiment, the hair care composition further comprises one or more additional benefit agents. The benefit agents comprise a material selected from the group consisting of anti-dandruff agents, anti-fungal agents, anti-itch agents, anti-bacterial agents, anti-microbial agents, moisturization agents, anti-oxidants, vitamins, lipid soluble vitamins, perfumes, brighteners, enzymes, sensates, attractants, dyes, pigments, bleaches, and mixtures thereof.

The hair care compositions of the present invention may be presented in typical hair care formulations. They may be in the form of solutions, dispersion, emulsions, powders, talcs, encapsulated, spheres, spongers, solid dosage forms, foams, and other delivery mechanisms. The compositions of the embodiments of the present invention may be hair tonics, leave-on hair products such as treatment, and styling products, rinse-off hair products such as shampoos, and treatment products; and any other form that may be applied to hair.

According to one embodiment, the hair care compositions may be provided in the form of a porous, dissolvable solid structure, such as those disclosed in U.S. Patent Application Publication Nos. 2009/0232873; and 2010/0179083, which are incorporated herein by reference in their entirety. Accordingly, the hair care compositions comprise a chelant, a buffer system comprising an organic acid, from about 23% to about 75% surfactant; from about 10% to about 50% water soluble polymer; and optionally, from about 1% to about 15% plasticizer; such that the hair care composition is in the form of a flexible porous dissolvable solid structure, wherein said structure has a Percent open cell content of from about 80% to about 100%.

According to another embodiment, the hair care compositions may be in the form of a porous dissolvable solid structure comprising a chelant; a buffer system comprising an organic acid from about 23% to about 75% surfactant; wherein said surfactant has an average ethoxylate/alkyl ratio of from about 0.001 to about 0.45; from about 10% to about 50% water soluble polymer; and from about 1% to about 15% plasticizer; and wherein said article has a density of from about 0.03 g/cm$^3$ to about 0.20 g/cm$^3$.

According to another embodiment, the hair care compositions may be in the form of a viscous liquid comprising a chelant; a buffer system comprising an organic acid from 5-20% surfactant and a polycarboxylate rheology modifier; wherein the polycarboxylate is specifically chosen to be effective at the high electrolyte levels resulting from the incorporation of the key buffer system and chelant used for this invention. Non-limiting examples include acrylates/ C10-C30 alkyl acrylate crosspolymers such as Carbopol EDT2020, 1342,1382, etc. from Lubrizol. Rheology benefits of these actives in our embodiments include stability, ease of dispensing, smoothness of spreading, etc.

The hair care compositions are generally prepared by conventional methods such as are known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The hair care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

Penetration of Moisture Control Material Inside the Hair

In an embodiment of the present invention, compositions can comprise of glycols, polyglycols, urea, ethers or mixture thereof. These materials increase penetration of moisture control actives such as salicylic acid, 5-chloro salicylic acid, improving their performance. Propylene glycol, butylene glycol and other glycols, increase penetration of 5-chlorosalicylic acid inside hair as it acts as carrier for the actives to penetrate further. As active penetration increases, there is an increase in efficacy of the active, i.e. there is increase in % water reduction as shown below in Table 5. Table 5 shows the amount of 5-chlorosalicylic acid that penetrates inside oxidatively damaged hair after hair treatment with two different compositions. It also shows the % water reduction observed after the treatment versus treatment with control leave-on treatment compositions. These results demonstrate that 5-chlorosalicylic acid penetrates 4 times more in the presence of propylene glycol and there is an increase in % water reduction as measured by DVS of approximate 4 times more than without propylene glycol. Another example of material that enhances the penetration of moisture control material is 2-hydroxyethyl urea. Leave on treatment composition that contain 2% of 2-hydroxyethyl urea increases the penetration of salicylic acid inside hair by 14% compared to the corresponding composition that does not contain 2-hydroxyethyl urea (see example III and IV).

Enhancing of hair penetration of Moisture Control Material in oxidatively damaged (bleached) Caucasian hair

| Raw Material | Control | Formula Example | | | |
| --- | --- | --- | --- | --- | --- |
| | | I | II | III | IV |
| Distilled Water | 50.0% | 48.93% | 43.9% | 48.93% | 48.00% |
| Ethanol | 50.0% | 48.93% | 43.9% | 48.93% | 48.00% |
| 5-Chlorosalicylic acid | 0.0% | 2.0% | 2.0% | 0.0% | 0.0% |
| 2-hydroxyethyl urea | 0.0% | 0.0% | 0.0% | 0.0% | 2.0% |
| Salicylic acid | 0.0% | 0.0% | 0.0% | 2.0% | 2.0% |
| 2,4-Dihydroxybenzoic acid | 0.0% | 0.15% | 0.15% | 0.0% | 0.0% |
| Propylene glycol | 0.0% | 0% | 10% | 0% | 0.0% |
| Composition pH adjusted to | 4.2 | 4.2 | 4.2 | 4.2 | 4.2 |
| % Water Reduction versus control treatment | — | 0.67% | 3% | — | — |
| Amount of 5-chlorosalicylic acid inside the hair (mg/g of hair) | — | 1 | 3.97 | — | — |
| Amount of Salicylic acid inside hair (mg/g of hair) after 5 cycles | — | — | — | 4.7 | 5.6 |

The penetration amount of 5-chlorosalicylic acid is determined using the following protocol. Each hair tress is extracted 3 times with 0.1% TFA (Trifluoroacetic acid) in methanol and the individual extracts are analyzed separately using HPLC method.

In addition to the increase of the penetration amount of the moisture control material, the presence of glycol in the composition prevents the crystallization of part of the moisture control material in the surface of the hair. Such crystallization causes a non-smooth, negative hair feel, which may be perceived by consumers as hair damage or lack of conditioning.

It has been observed that in an embodiment of the present invention the presence of propylene glycol may provide penetration enhancement for Molecular Class I and Class II materials.

Anti-Dandruff Actives

In an embodiment of the present invention, the compositions may contain anti-dandruff agents. When present in these compositions, the anti-dandruff agent is typically included in an amount of about 0.01 wt. % to about 5 wt. %, based on the total weight of the personal care composition. In these compositions, the anti-dandruff particulate should be physically and chemically compatible with other ingredients of the composition, and should not otherwise unduly impair product stability, aesthetics, or performance.

Anti-dandruff agents suitable for use in personal care compositions include pyridinethione salts, azoles (e.g., ketoconazole, econazole, and elubiol), selenium sulfide, particulate sulfur, salicylic acid, and mixtures thereof. A typical anti-dandruff agent is pyridinethione salt. Personal care compositions can also include a zinc-containing layered material. An example of a zinc-containing layered material can include zinc carbonate materials. Of these, zinc carbonate and pyridinethione salts (particularly zinc pyridinethione or "ZPT") are common in the composition, and often present together.

In addition to the anti-dandruff active, compositions may also include one or more anti-fungal or anti-microbial actives in addition to the metal pyrithione salt actives. Suitable anti-microbial actives include coal tar, sulfur, charcoal, whitfield's ointment, castellani's paint, aluminum chloride, gentian violet, octopirox (piroctone olamine), ciclopirox olamine, undecylenic acid and it's metal salts, US 2011/0305778 A1 Dec. 15, 2011 potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Typical anti-microbials include itraconazole, ketoconazole, selenium sulphide and coal tar.

Zinc-Containing Material, Including Zinc Carbonate

In an embodiment of the present invention, compositions may include a zinc-containing layered material. Those compositions can include about 0.001 wt. % to about 10 wt. % of the zinc-containing layered material based on the total weight of the personal care composition. In an embodiment of the present invention, a personal care composition can include a zinc-containing layered material from about 0.01 wt. % to about 7 wt. % based on the total weight of the personal care composition. In yet a further embodiment of the present invention, a personal care composition can include a zinc-containing layered material from about 0.1 wt. % to about 5 wt. %, based on the total weight of the composition. Suitable zinc-containing layered materials include those described below, including zinc carbonate materials, which are presently preferred:

Zinc-containing layered structures are those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975) Zinc-containing layered materials (ZLM's) may have zinc incorporated in the layers and/or be components of the gallery ions.

Many ZLM's occur naturally as minerals. Common examples include hydrozincite (zinc carbonate hydroxide), basic zinc carbonate, aurichalcite (zinc copper carbonate hydroxide), rosasite (copper zinc carbonate hydroxide) and many related minerals that are zinc-containing. Natural ZLM's can also occur wherein anionic layer species such as clay-type minerals (e.g., phyllosilicates) contain ion-exchanged zinc gallery ions. All of these natural materials can also be obtained synthetically or formed in situ in a composition or during a production process.

These classes of ZLM's represent relatively common examples of the general category and are not intended to be limiting as to the broader scope of materials which fit this definition.

Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union US 2011/0305778 A1 Dec. 15, 2011 Ld Corp.: New York, N.Y., USA), Zinc Carbonate (Elementis Pigments: Durham, UK), and Zinc Carbonate AC (Bruggemann Chemical: Newtown Square, Pa., USA).

Optional Ingredients

The compositions of the present invention can also additionally comprise any suitable optional ingredients as desired. For example, the composition can optionally include other active or inactive ingredients.

The compositions may include other common hair ingredients such as other anti-dandruff actives, minoxidil, conditioning agents, and other suitable materials. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, rheology modifiers, hair conditioning agents, and surfactants.

The formulations of the present invention may be present in typical hair care compositions. They may be in the form of solutions, dispersion, emulsions, powders, talcs, encapsulated, spheres, spongers, solid dosage forms, foams, and other delivery mechanisms. The composition of the present invention may be hair tonics, leave-on hair products such as conditioners, treatment, and styling products, and any other form that may be applied to the hair.

Formulations and Examples

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

Leave-on Hair Treatment Protocol:

An amount of 0.20 g of each composition of Examples I to IV is spread via a syringe onto separate natural virgin brown hair switches weighing 2.0 g (dosage 0.10 g of solution per g of hair). The hair is allowed to air dry and then analyzed using the DVS method described above. The experiment is repeated for a dosage of 0.50 g of solution per g of hair. The hair in this case is also assessed by expert graders, as described below, in addition to the DVS analysis.

DVS Measurement:

An amount of 25-30 mg of hair with length of approximately 1 cm is weighed and hold for equilibration at 0% RH for 16 hours. After the 16-hour period, the RH is increased to 10% and maintained at this level for 6 hours. Then, the RH is increased by 10% after every 6 hours interval until it reaches 90% RH. The % water reduction is calculated as follows:

A=Amount of water absorbed by the hair treated with composition containing the Moisture Control Material B=Amount of water absorbed by the hair treated with control composition (only carrier) containing no Moisture Control Material % Water reduction=$[(B-A) \times 100]/B$ Hair Switch Feel Assessment Method: The treated hair switches are kept at high humidity (above 85% RH) for 2 hrs and then ten expert graders are asked to rate each of them in terms of tactile feel based on a 5 point scale, 5 being the highest (best feel) and 1 being the lowest rating.

Leave-on Treatment Formulation:

| | Formula Example | | | | | | | |
|---|---|---|---|---|---|---|---|---|
| Raw Material | Leave-on treatment Control (wt./wt.) % | I (wt./wt.) % | II (wt./wt.) % | III (wt./wt.) % | IV (wt./wt.) % | V (wt./wt.) % | VI (wt./wt.) % | VII (wt./wt.) % |
| Distilled Water | QS | QS | QS | QS | QS | QS | QS | QS |
| Ethanol | 50.00 | 50.00 | 50.00 | 50.00 | 50.00 | 50.00 | 50.00 | 50.00 |
| Polyacrylamide & C13-14 Isoparaffin & Laureth-7 (Sepigel 305) | 1.85 | 1.85 | 1.85 | 1.85 | 1.85 | 1.85 | 1.85 | 1.85 |
| Perfume | 0.46 | 0.46 | 0.46 | 0.46 | 0.46 | 0.46 | 0.46 | 0.46 |
| Salicylic acid | 0 | 2.0 | 0 | 0 | 2.0 | 2.0 | 0.0 | 0.0 |
| 5-Chlorosalicylic acid | 0 | 0 | 2.0 | 0 | 0 | 0 | 2.0 | 2.0 |
| 2,4-Dihydroxybenzoic acid | 0 | 0 | 0 | 2.0 | 0.15 | 0.15 | 0.15 | 0.15 |
| Oleic acid | 0 | 0 | 0 | 0 | 0 | 0.25 | 0 | 0.25 |
| 2-Hexyl-1-decanol | 0 | 0 | 0 | 0 | 0 | 0.25 | 0 | 0.25 |
| Final pH | 4.2 | 4.2 | 4.2 | 4.2 | 4.2 | 4.2 | 4.2 | 4.2 |
| % Water Reduction versus Leave-on Treatment Control at dose of 0.10 g of composition for 1.0 g of hair | '— | — | — | — | 4 | 5 | 5 | 7 |
| % Water Reduction versus Leave-on Treatment Control at dose of 0.50 g of composition for 1.0 g of hair. Control is dosed at 0.50 g of composition for 1.0 g of hair | — | 4 | 5 | 5 | 9 | 8 | 10 | 10 |
| Feel Rating Leave-on Treatment Control at dose of 0.10 g of composition for 1.0 g of hair | 1 | 1 | 2 | 2 | 2 | 3 | 2 | 4 |

| | Formula Example | | | | | |
|---|---|---|---|---|---|---|
| Raw Material | VIII | IX | X | XI | XII | XIII |
| Distilled Water | QS | QS | QS | QS | QS | QS |
| Ethanol | 50.0 | 50.0 | 50.0 | 50.0 | 50.0 | 50.0 |
| 5-Chlorosalicylic acid | 1.0 | | | 1.0 | 1.0 | 1.0 |
| 2-Hexyl-1-decanol | | | 5.0 | 5.0 | | 5.0 |
| Isostearyl isostearate | | 2.0 | | | 2.0 | 2.0 |
| Final pH | 4 | 4 | 4 | 4 | 4 | 4 |
| % Water Reduction versus Leave-on Treatment Control at dose of 0.10 g of composition for 1.0 g of hair | 1.3 | 0.7 | 1.0 | 2.0 | 1.4 | 3.0 |
| Feel Rating (on 5 scale point with 5 as highest and 1 as lowest) | 1 | 2 | 2 | 3 | 3 | 4 |

Results:

Formula I to XIII showed % water reduction at high humidity. Higher % water reductions are observed in hair treated with higher doses of leave-on Formulas I-XIII
The feel assessment results indicate that combinations of
  (a) 5-Chlorosalicylic acid and 2-hexyl-1-decanol;
  (b) 5-Chlorosalicylic acid and isostearyl isostearate;
  (c) 5-Chlorosalicylic acid and 2-hexyl-1-decanol and isostearyl isostearate provide, not only water absorption reduction (resulting in frizz benefit), but also tactile feel benefit. This is shown by the feel comparisons of (a) Example XI versus Examples VIII and IX, (b) Example XII versus Examples VIII and X, and (c) Example XIII versus Examples VIII, IX and X.

Additional Evaluations

Additional leave-on treatment compositions are prepared (Tables 1 and 2) according to the procedure described above, which are used to treat hair switches using the procedure described above (amount of 0.10 g of composition per g of hair). The switch is kept at high humidity (above 85%) for 2 hours. Then, ten experts are asked to rate each hair switch in terms of frizz, clean feel, and greasy feel, based on a 5 point scale, 5 being the highest and 1 being the lowest rating.
Acceptable values are:
For frizz, less than 2 (lower number corresponds to less frizz);
For no greasy feel less than 3, (lower number corresponds to less greasy feel), and
For clean feel greater than 3 (higher number corresponds to cleaner feel).

TABLE 1

Class I Compounds

| Raw Material | Formula Example | | | | | |
|---|---|---|---|---|---|---|
| | Control | XIV | XV | XVI | XVII | XVIII |
| Distilled Water | 50.0% | 49.5% | 49.5% | 49.5% | 49.5% | 49.5% |
| Ethanol | 50.0% | 49.5% | 49.5% | 49.5% | 49.5% | 49.5% |
| 5-Chlorosalicylic acid | 0% | 1% | 0% | 0% | 0% | 0% |
| Salicylic acid | 0% | 0% | 1% | 0% | 0% | 0% |
| 4-Hydroxybenzenesulphonic acid | 0% | 0% | 0% | 1% | 0% | 0% |
| 2,4-Dihydroxybenzoic acid | 0% | 0% | 0% | 0% | 1% | 0% |
| Terminal Amino Silicone | 0% | 0% | 0% | 0% | 0% | 1% |
| Composition pH adjusted to | 4.2 | 4.2 | 4.2 | 4.2 | 4.2 | 4.2 |
| Greasy Feel | 2 | 1 | 2 | 2 | 2 | 4 |
| Frizz | 4 | 2 | 1 | 2 | 2 | 3 |
| Clean Feel | 4 | 4 | 3 | 4 | 4 | 1 |

Results of Hair Switch Rating from Class I Molecules:

Molecules (5-chlorosalicylic acid, salicylic acid, 4-hydroxybenzenesulphonic acid, 2,4-dihydroxybenzoic acid) from Class I provide hair benefits. More specifically, Table 1 shows that hair treatments with 5-chlorosalicyclic acid, salicylic acid, 4-hydroxybenzenesulfonic acid and 2,4-dihydroxybenzoic acid provide fizz protection with clean feel and without greasy feel negative, as opposed to treatment with terminal aminosilicone, which provide some frizz benefit but with greasy feel negative and significantly less clean feel.

TABLE 2

Class II Compounds

| Raw Material | Formula Example | | | | | |
|---|---|---|---|---|---|---|
| | Control | XIX | XX | XXI | XXII | XXIII |
| Distilled Water | 50.0% | 49.5% | 49.5% | 49.5% | 49.5% | 49.5% |
| Ethanol | 50.0% | 49.5% | 49.5% | 49.5% | 49.5% | 49.5% |
| Isostearyl isostearate | 0% | 1% | 0% | 0% | 0% | 0% |
| 2-Hydroxyethyl salicylate | 0% | 0% | 1% | 0% | 0% | 0% |
| Octyl salicylate | 0% | 0% | 0% | 1% | 0% | 0% |
| 2-Hexyl-1-decanol | 0% | 0% | 0% | 0% | 1% | 0% |
| Terminal Amino Silicone | 0% | 0% | 0% | 0% | 0% | 1% |
| Composition pH adjusted to | 4.2 | 4.2 | 4.2 | 4.2 | 4.2 | 4.2 |
| Greasy Feel | 2 | 2 | 2 | 2 | 3 | 4 |
| Frizz | 4 | 2 | 2 | 1 | 1 | 3 |
| Clean Feel | 4 | 3 | 3 | 3 | 3 | 1 |

Results of Hair Switch Rating from Class II Molecules:

Molecules (Isostearyl isostearate, 2-hydroxylethyl salicylate, octyl salicylate, 2-hexyl-1-decanol) from Class II provide hair benefits. More specifically, Table 2 shows that hair treatment with isostearyl isostearate, 2-hydroxyethyl salicylate, octyl salicylate, and 3-hexyl-1-decanol provide frizz protection with clean feel and without greasy feel negative, as opposed to treatment with terminal aminosilicone, which provide some frizz benefit but with greasy feel negative and significantly less clean feel.

Evaluation of Hair Friction

Leave-on formulation containing Moisture Control Material and Silicone oil shows improvement in dry feel compared to untreated hair. This is concluded by measurement of dry hair friction. For this evaluation, natural virgin brown hair switches (4.0 g) are washed with clarifying shampoo, and then treated with leave-on treatment of composition XXIV according to the protocol described above. Before the evaluation, the switches are air dried overnight in a controlled temperature and humidity room (22° C./50% RH). The friction force (grams) between the hair surface and a urethane pad along the hair is measured, with three measurements per switch using an Instron Tester instrument (Instron 5542, Instron, Inc, Canton, Mass., USA).

TABLE 3

Hair Friction

| Raw Material | Formula Example XXIV | Control Hair - No Treatment |
|---|---|---|
| Distilled Water | 49.5% | |
| Ethanol | 49.5% | |
| 2,4 dihydroxybenzoic acid | 1% | |
| Silicone oil | 0% | |
| Composition pH adjusted to | 4.2 | |
| Average Force (g) | 40 | 55 |

As Table 3 indicates, treatment of hair with leave-on composition containing Moisture Control material and silicone oil results in reduced hair friction, which indicates improved dry feel.

It is known that organic hydrophobic molecules that are naturally present inside the hair (e.g. as part of Cell Membrane Complex lipids) contribute to its strength and integrity. It is also known that cosmetic treatments, such as oxidative coloring and permanent shaping result in reduction of the concentration of such hydrophobic material from hair. Thus, penetration of hydrophobic materials (e.g. Class II materials) inside the hair can contribute to lipid replenishment, which, at the same time, reduces water uptake to deliver moisture or frizz control benefit. Combination of different Class II materials e.g. benzyl alcohol, 2-hexyl-1-decanol, isostearyl isostearate, have multi-functionality of penetration, getting embedded into lipid of hair and also increasing the penetration of other hydrophobic materials like oleic resulting in further increase hydrophobicity of the hair interior.

Experimental Section—Regimen

Formulations and Examples

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

EXAMPLES

Shampoo Composition Preparation:

The shampoo composition delivers consumer desired shampooing in addition to preventing water uptake inside the hair at high humidity.

The shampoo composition comprises from about 0.2% to about 10%, alternatively from about 1% to about 7%, alternatively from about 2% to about 5% of a compound selected from the group consisting of Moisture Control Material Molecular Class I e.g. Salicylic acid, 2, 4 dihydroxybenzoic acid etc. and/or Moisture Control Material Molecular Class II e.g. 2-hexyldecanol, Isostearyl Isostearate etc. and mixtures thereof, by weight of the shampoo composition. After applying to the hair a shampoo composition as described herein, the method then comprises rinsing the shampoo composition from the hair.

Rinse-Off Conditioner Composition Preparation:

The rinse-off conditioner compositions can be prepared by any conventional method well known in the art. The cationic surfactants and the fatty alcohols are mixed together and heated to from about 66° C. to about 85° C. to form an oil phase. Separately, the disodium EDTA, the Methylchloroisothiazolinone (preservative) and the water are mixed and heated to from about 20° C. to about 48° C. to form an aqueous phase. The oil phase is mixed into the water phase under high shear to form the gel matrix. The remaining of the components are added into the gel matrix with agitation. Then, the composition is cooled down to room temperature.

Deep Conditioning Treatment Preparation:

The Moisture Control Materials are added into aqueous solution to which Polyethylene glycol-40 hydrogenated castor oil is added as suspending agent and pH of solution is adjusted to final pH of 4.2. Alternatively, moisture control materials may be added into the cationic surfactants and the fatty alcohols are mixed together and heated to from about 66° C. to about 85° C. to form an oil phase. Separately, the disodium EDTA, the Methylchloroisothiazolinone (preservative) and the water are mixed and heated to from about 20° C. to about 48° C. to form an aqueous phase. The oil phase is mixed into the water phase under high shear to form the gel matrix. The remaining of the components are added into the gel matrix with agitation. Then, the composition is cooled down to room temperature. The solution pH is adjusted with sodium hydroxide (50% w/w) to a final pH of 4.2.

Soaking Treatment Preparation:

The Moisture Control Material is added into a 50:50 ethanol:water solvent at a concentration of 2% w/w and mixed until completely dissolved. The solution pH is adjusted with sodium hydroxide (50% w/w) to a final pH of 4.2. The soaking solution is kept at 40 deg C. for 2 hrs until a uniform composition is obtained.

Leave-on Treatment Composition Preparation:

The leave-on treatment compositions are prepared by adding the Moisture Control Materials and perfume, if needed, into a 50:50 ethanol/water carrier and stirred until complete dissolution. The solution pH is adjusted using sodium hydroxide (50% w/w) to a final pH of 4.0-4.2. The Sepigel 305 is then added, if needed, and the solution is mixed using a high-speed-mixer for 2-5 minutes at 1800-2300 rpm until a uniform composition is obtained.

Shampoo Hair Treatment Protocol:

All testing are performed on Virgin Caucasian Hair weighing approximately 2.0 grams and having a length of approximately 6 inches. The hair switches are commercially available from IHIP (International Hair Importers). Three hair switches 1 per rinse-off compositions per dosage are used. Each hair switch is washed with clarifying shampoo followed by a treatment with the rinse-off conditioner according to the following protocol. An amount of 0.40 g of shampoo is spread via a syringe onto separate hair switch. That is, the dosage is 0.20 g of shampoo per g of hair. Each application consists of adding shampoo to the hair, milking for 30 seconds followed by rinsing for 30 seconds. Shampoo is then reapplied (0.1 g/g), milked for 30 seconds and rinsed for 30 seconds. Excess water is squeezed from the hair switches.

Deep Conditioning Treatment Protocol:

Wet hair switch is treated with Dosage (D: dosage applied on hair)≥0.2 g/g in solution for treatment time (T: time of treatment) varying from 1 min 2 hours at room temperature. After application hair is either rinsed/dried or followed by next step of product application. Specific dosage and treatments examples are captured in Table 12.

Soaking Treatment Protocol:

One hair switch of natural virgin brown hair is placed in 200 ml of this solution for 2 hours in an oven set at 40° C. After the 2-hour period, the hair is removed, either air dried, blow dried or rinsed or followed by next step of product application Rinse-Off Conditioner Hair Treatment Protocol:

All testing are performed after shampoo treatment, excess of water squeezed from the hair switches and then 0.2 g/g of the rinse-off conditioner is applied and milked for 30 seconds and then rinsed for 30 seconds.

Leave-on Hair Treatment Protocol:

Last step in regimen, is a leave-on treatment, where-in an amount of 0.20 g of each composition is spread via a syringe onto separate natural virgin brown hair switches weighing 2.0 g (dosage 0.10 g of solution per g of hair). The hair is allowed to air dry and then analyzed using the DVS method described below. The hair in this case is also assessed by expert graders, as described below, in addition to the DVS analysis.

Evaluation Methods

The hair switches that are treated with the regimen compositions are evaluated using the following methodologies.

DVS Measurement:

An amount of 25-30 mg of hair with length of approximately 1 cm is weighed and hold for equilibration at 0% RH for 16 hours. After the 16-hour period, the RH is increased to 10% and maintained at this level for 6 hours. Then, the RH is increased by 10% after every 6 hours interval until it reaches 90% RH. The % water reduction is calculated as follows:

A=Amount of water absorbed by the hair treated with composition containing the Moisture Control Material
B=Amount of water absorbed by the hair treated with control composition (only carrier) containing no Moisture Control Material $$\% \text{ Water reduction} = [(B-A) \times 100]/B$$

The standard error for DVS measurement is less than 0.05 a. Determination of Frizz Reduction

The hair switches are thoroughly blow-dried after the treatment with rinse-off conditioner while holding the hair switch with all the hair fibers at the tip and then the hair switches are heat straightened by sectioning the hair into three parts and then heat with flat iron for 8 passes at 400-450 F. Hair switches are then kept at low humidity (between 20-25% RH) for equilibration for at least an hour. After the equilibration period, the hair switches are transferred to high humidity chamber (85-90% RH) for frizz assessment. Image of hair switches using a NIR Camera with parallel polarizers and are taken immediately after insertion of the hair into the high humidity chamber ($t_0$). Another image is taken after 3 hours ($t_{3h}$). The pixels are analyzed (selecting the entire hair switch) for 2D projection of volume (using vncviewer software). Then, the mean projected area is determined for the hair switch at to ($A_{t0}$) and for the hair at $t_{3h}$ ($A_{t3h}$) and the frizz calculated using the equation given below. Each experiment is repeated with 3 hair switches. The percent Frizz is calculated using below equation:

$$\% \text{ Frizz} = 100 \times (A_{t3h} - A_{t0}/A_{t0})$$

$$\% \text{ Frizz reduction} = 100 \times (\% \text{ Frizz(present invention composition)} - \% \text{ Frizz(control composition}/\% \text{ Frizz(control composition)}).$$

The standard error for Frizz measurement is less than 0.1
Correlation of % Frizz Reduction Vs % Water Reduction Determined by DVS Methodology Results obtained from DVS measurements and the results from the determination of the frizz reduction methodology of various switches indicate that there is a correlation between the two methods. In other words, hair switches that show low water reduction also show lower frizz as shown in FIG. 1.

FIG. 1 depicting correlation of % water reduction vs % frizz reduction, where hair switches with different dosage are treated and their % water reduction and % frizz reduction is measured using DVS and frizz method respectively.

FIG. 1 is a plot depicting that there is a monotonic correlation between % water reduction and % frizz reduction. As material dosage increases, % water reduction increase resulting in increase in % frizz reduction i.e. more frizz control.

Results

As FIG. 1 demonstrates, there is a monotonic correlation between % water reduction and % frizz reduction. As material dosage increases, more material penetrates into hair, The % water reduction at high humidity increases resulting in an increase in % frizz reduction i.e. more frizz control. This confirms the present invention's technical hypothesis of material penetration, interaction with hair protein and decrease of water uptake inside hair at high humidity resulting in frizz control.

Hair Switch Feel Assessment Method:

The treated hair switches are kept at high humidity (above 85% RH) for 2 hrs and then ten expert graders are asked to rate each of them in terms of tactile feel based on a 5 point scale, 5 being the highest (best feel) and 1 being the lowest rating.

TABLE 1

Shampoo Formulation:

| Raw Material | Shampoo Control A (wt./wt.) % | Shampoo Example I (wt./wt.) % | Shampoo Example II (wt./wt.) % | Shampoo Example III (wt./wt.) % | Shampoo Example IV (wt./wt.) % | Shampoo Example V (wt./wt.) % | Shampoo Example VI (wt./wt.) % | Shampoo Example VII (wt./wt.) % | Shampoo Example VIII (wt./wt.) % |
|---|---|---|---|---|---|---|---|---|---|
| Water Purified | Q.S to 100 | Q.S to 100 | Q.S to 100 | Q.S to 100 | Q.S to 100 | Q.S to 100 | Q.S to 100 | Q.S to 100 | Q.S to 100 |
| Sodium Laureth 3 Sulfate 28% solution | 21.6 | 21.6 | 21.6 | 21.6 | 21.6 | 21.6 | 21.6 | 21.6 | 21.6 |
| Sodium Lauryl Sulfate 29% solution | 34.5 | 34.5 | 34.5 | 34.5 | 34.5 | 34.5 | 34.5 | 34.5 | 34.5 |
| Laureth-4 | 0.9 | 0.9 | 0.9 | 0.9 | 0.9 | 0.9 | 0.9 | 0.9 | 0.9 |

TABLE 1-continued

Shampoo Formulation:

| Raw Material | Shampoo Control A (wt./wt.) % | Shampoo Example I (wt./wt.) % | Shampoo Example II (wt./wt.) % | Shampoo Example III (wt./wt.) % | Shampoo Example IV (wt./wt.) % | Shampoo Example V (wt./wt.) % | Shampoo Example VI (wt./wt.) % | Shampoo Example VII (wt./wt.) % | Shampoo Example VIII (wt./wt.) % |
|---|---|---|---|---|---|---|---|---|---|
| Dimethicone 330M cps | 0.5 | 0.5 | 0.5 | 0.5 | 0.5 | 0.5 | 0.5 | 0.5 | 0.5 |
| Glycol Distearate | 1.5 | 1.5 | 1.5 | 1.5 | 1.5 | 1.5 | 1.5 | 1.5 | 1.5 |
| Polyquaternium-6 | 0.32 | 0.32 | 0.32 | 0.32 | 0.32 | 0.32 | 0.32 | 0.32 | 0.32 |
| Trisodium ethylenediamine disuccinate | 0 | 0 | 0 | 0 | 0 | 0 | 0 | 0 | 0 |
| Sodium Benzoate | 0.27 | 0.27 | 0.27 | 0.27 | 0.27 | 0.27 | 0.27 | 0.27 | 0.27 |
| Citric acid 50% Solution | 0.52 | 0.52 | 0.52 | 0.52 | 0.52 | 0.52 | 0.52 | 0.52 | 0.52 |
| Methylchloroisothiazolinone/methylisothiazolinone | 0.035 | 0.035 | 0.035 | 0.035 | 0.035 | 0.035 | 0.035 | 0.035 | 0.035 |
| Sodium chloride | 1.66 | 1.66 | 1.66 | 1.66 | 1.66 | 1.66 | 1.66 | 1.66 | 1.66 |
| Fragrance | 0.65 | 0.65 | 0.65 | 0.65 | 0.65 | 0.65 | 0.65 | 0.65 | 0.65 |
| DL-Panthenol 56% solution | 0.05 | 0.05 | 0.05 | 0.05 | 0.05 | 0.05 | 0.05 | 0.05 | 0.05 |
| Panthenyl Ethyl ether | 0.03 | 0.03 | 0.03 | 0.03 | 0.03 | 0.03 | 0.03 | 0.03 | 0.03 |
| Glycol Distearate | 1.5 | 1.5 | 1.5 | 1.5 | 1.5 | 1.5 | 1.5 | 1.5 | 1.5 |
| Salicylic acid[8] | 0 | 1.0 | 0.0 | 0.0 | 0.0 | 0.0 | 0 | 1 | 1 |
| 5-Chloro Salicylic acid[9] | 0 | 0 | 1.0 | 0 | 0 | 0 | 0 | 0 | 0 |
| 2,4 dihydroxybenzoic acid[10] | 0 | 0 | 0 | 1 | 0 | 0 | 0 | 0.15 | 0 |
| Isostearyl Isostearate[11] | 0 | 0 | 0 | 0 | 1 | 0 | 0 | 1 | 1 |
| 2-hexyldecanol[12] | 0 | 0 | 0 | 0 | 0 | 1 | 0 | 5 | 5 |
| Oleic acid[13] | 0 | 0 | 0 | 0 | 0 | 0 | 0.2 | 0 | 0.2 |
| % Water Reduction versus Control at dose of 0.2 g of composition for 1 g of hair | — | 0.6 | 0.8 | 0.3 | 0.4 | 0.6 | 0.1 | 1.2 | 2 |

TABLE 2

Rinse-off Conditioner Formulations

| Raw Material | Active % | Conditioner Control A (wt./wt.) % | Conditioner Example IX (wt./wt.) % | Conditioner Example X (wt./wt.) % | Conditioner Example XI (wt./wt.) % | Conditioner Example XII (wt./wt.) % | Conditioner Example XIII (wt./wt.) % | Conditioner Example XIV (wt./wt.) % | Conditioner Example XV (wt./wt.) % | Conditioner Example XVI (wt./wt.) % |
|---|---|---|---|---|---|---|---|---|---|---|
| Benzenemethanaminium, N,N,N-trimethyl-, chloride (BTMAC)/Isopropyl Alcohol (IPA)[1] | 80 | 2.848 | 2.848 | 2.848 | 2.848 | 2.848 | 2.848 | 2.848 | 2.848 | 2.848 |
| Cetyl Alcohol[2] | 90 | 1.857 | 1.857 | 1.857 | 1.857 | 1.857 | 1.857 | 1.857 | 1.857 | 1.857 |
| Stearyl Alcohol[3] | 97 | 4.643 | 4.643 | 4.643 | 4.643 | 4.643 | 4.643 | 4.643 | 4.643 | 4.643 |
| Benzyl Alcohol[4] | 99 | 0.400 | 0.400 | 0.400 | 0.400 | 0.400 | 0.400 | 0.400 | 0.400 | 0.400 |
| Disodium EDTA, Dihydrate[5] | 99 | 0.127 | 0.127 | 0.127 | 0.127 | 0.127 | 0.127 | 0.127 | 0.127 | 0.127 |
| Methylchloroisothiazolinone (Kathon CG)[6] | 1.5 | 0.033 | 0.033 | 0.033 | 0.033 | 0.033 | 0.033 | 0.033 | 0.033 | 0.033 |
| Terminal Amino Silicone[7] | 90-100 | 0.3 | 0.3 | 0.3 | 0.3 | 0.3 | 0.3 | 0.3 | 0.3 | 0.3 |
| Perfume | | 0.550 | 0.550 | 0.550 | 0.550 | 0.550 | 0.550 | 0.550 | 0.550 | 0.550 |
| Salicylic acid[8] | 99.5 | 0 | 1.0 | 0.0 | 0.0 | 0.0 | 0.0 | 0 | 1 | 1 |
| 5-Chloro Salicylic acid[9] | 98 | 0 | 0 | 1.0 | 0 | 0 | 0 | 0 | 0 | 0 |
| 2,4 dihydroxybenzoic acid[10] | 97 | 0 | 0 | 0 | 1 | 0 | 0 | 0.15 | 0 | 0 |
| Isostearyl Isostearate[11] | 100 | 0 | 0 | 0 | 0 | 1 | 0 | 0 | 1 | 1 |
| 2-hexyldecanol[12] | 97 | 0 | 0 | 0 | 0 | 0 | 5 | 0 | 5 | 5 |
| Oleic acid[13] | 78 | 0 | 0 | 0 | 0 | 0 | 0 | 0.2 | 0 | 0.2 |

TABLE 2-continued

Rinse-off Conditioner Formulations

| Raw Material | Active % | Conditioner Control A (wt./wt.) % | Conditioner Example IX (wt./wt.) % | Conditioner Example X (wt./wt.) % | Conditioner Example XI (wt./wt.) % | Conditioner Example XII (wt./wt.) % | Conditioner Example XIII (wt./wt.) % | Conditioner Example XIV (wt./wt.) % | Conditioner Example XV (wt./wt.) % | Conditioner Example XVI (wt./wt.) % |
|---|---|---|---|---|---|---|---|---|---|---|
| Purified Water | | Q.S. | Q.S. | Q.S. | Q.S. | Q.S. | Q.S. | Q.S. | Q.S. | Q.S. |
| % Water Reduction versus Control at dose of 0.2 g of composition for 1 g of hair | | — | 0.6 | 0.8 | 0.2 | 0.8 | 0.9 | 0.1 | 2 | 3 |
| % Frizz Reduction | | | 7.69 | 7.79 | 7.48 | 7.79 | 7.84 | 7.43 | 8.41 | 8.93 |

[1] Supplied by Feixiang Chemicals (Zhangjingang) Co., Ltd.
[2] Supplied by P&G Chemicals
[3] Supplied by P&G Chemicals
[4] Supplied by Ineos Maastricht BV (Maastricht NL)
[5] Trilon BD Powder supplied by BASF SE (Ludwigshafen, DE)
[6] Kathon CG supplied by Rohm & Haas Co (Philadelphia US)
[7] Y-14945 supplied by Momentive Performance Materials
[8] Supplied by API Corporation
[9] Supplied by Sigma Aldrich
[10] Supplied by Sigma Aldrich
[11] Crodamol ISIS supplied by Croda
[12] Isofol 16 supplied by Sasol (Brunsbuettel, DE)
[13] Greenolene 6928 supplied by Green Oleo

TABLE 3

Deep Conditioning Treatment Formulation:

| Raw Material | Deep treatment-Control A (wt./wt.) % | Example XVII (wt./wt.) % | Example XVIII (wt./wt.) % | Example XIX (wt./wt.) % | Example XX (wt./wt.) % | Example XXI (wt./wt.) % | Example XXII (wt./wt.) % | Example XXIII (wt./wt.) % | Example XXIV (wt./wt.) % | Example XXV (wt./wt.) % |
|---|---|---|---|---|---|---|---|---|---|---|
| Distilled Water | to 100 | to 100 | to 100 | to 100 | to 100 | to 100 | to 100 | to 100 | to 100 | to 100 |
| Polyethylene Glycol 40 Hydrogenated Castor Oil | 1.0 | 1.0 | 1.0 | 1.0 | 1.0 | 1.0 | 1.0 | 1.0 | 1.0 | 1.0 |
| Salicylic acid | 0 | 1 | 0 | 0 | 0 | 0 | 1.0 | 1.0 | 0 | 1.0 |
| 5 Chloro-Salicylic acid | 0 | 0 | 1 | 0 | 0 | 0 | 0 | 0 | 0 | 0 |
| 2,4-Dihydroxybenzoic acid | 0 | 0 | 0 | 1 | 0 | 0 | 0.15 | 0.15 | 0 | 0.15 |
| Isostearyl Isostearate | 0 | 0 | 0 | 0 | 1 | 0 | 0 | 2 | 0 | 0 |
| 2-Hexyl-1-decanol | 0 | 0 | 0 | 0 | 0 | 1 | 0 | 5 | 0 | 0 |
| Glyoxylic acid | 0 | 0 | 0 | 0 | 0 | 0 | 0 | 2 | 2 | 2 |
| Final pH | 4.2 | 4.2 | 4.2 | 4.2 | 4.2 | 4.2 | 4.2 | 4.2 | 4.2 | 4.2 |

TABLE 4

Soaking Formulation:

| Raw Material | Soaking treatment Control A (wt./wt.) % | Example XXVI (wt./wt.) % | Example XXVII (wt./wt.) % | Example XXVIII (wt./wt.) % | Example XXIX (wt./wt.) % | Example XXX (wt./wt.) % | Example XXXI (wt./wt.) % | Example XXXII (wt./wt.) % |
|---|---|---|---|---|---|---|---|---|
| Distilled Water | to 100 | to 100 | to 100 | to 100 | to 100 | to 100 | to 100 | to 100 |
| Ethanol | 50.0 | 50.0 | 50.0 | 50.0 | 50.0 | 50.00 | 50.0 | 50.0 |
| Salicylic acid | 0 | 2.0 | 0 | 0 | 2.0 | 0 | 0.0 | 0.0 |
| 5-Chlorosalicylic acid | 0 | 0 | 2.0 | 0 | 0 | 0 | 2.0 | 0 |

TABLE 4-continued

Soaking Formulation:

| Raw Material | Soaking treatment Control A (wt./wt.) % | Example XXVI (wt./wt.) % | Example XXVII (wt./wt.) % | Example XXVIII (wt./wt.) % | Example XXIX (wt./wt.) % | Example XXX (wt./wt.) % | Example XXXI (wt./wt.) % | Example XXXII (wt./wt.) % |
|---|---|---|---|---|---|---|---|---|
| 2,4-Dihydroxybenzoic acid | 0 | 0 | 0 | 2.0 | 0.15 | 0 | 0.15 | 0 |
| Oleic acid | 0 | 0 | 0 | 0 | 0 | 2 | 0 | 0 |
| 2-Hexyl-1-decanol | 0 | 0 | 0 | 0 | 0 | 0 | 0 | 2 |
| Final pH | 4.2 | 4.2 | 4.2 | 4.2 | 4.2 | 4.2 | 4.2 | 4.2 |
| Soaking Duration | 2 hours | 2 hours | 2 hours | 2 hours | 2 hours | 2 hours | 2 hours | 2 hours |
| % Water Reduction vs Soaking Treatment control | — | 32 | 30 | 35 | 24 | 12 | 28 | 12 |

TABLE 5

Leave-on Treatment Formulation

| Raw Material | Leave-on treatment Control A (wt./wt.) % | Example XXXIII (wt./wt.) % | Example XXXIV (wt./wt.) % | Example XXXV (wt./wt.) % | Example XXXVI (wt./wt.) % | Example XXXVII (wt./wt.) % | Example XXXVIII (wt./wt.) % | Example XXXIX (wt./wt.) % | Example XXXX (wt./wt.) % |
|---|---|---|---|---|---|---|---|---|---|
| Distilled Water | QS | QS | QS | QS | QS | QS | QS | QS | QS |
| Ethanol | 50.00 | 50.00 | 50.00 | 50.00 | 50.00 | 50.00 | 50.00 | 50.00 | 50.00 |
| Polyacrylamide & C13-14 Isoparaffin & Laureth-7 (Sepigel 305) | 1.85 | 1.85 | 1.85 | 1.85 | 1.85 | 1.85 | 1.85 | 1.85 | 1.85 |
| Perfume | 0.46 | 0.46 | 0.46 | 0.46 | 0.46 | 0.46 | 0.46 | 0.46 | 0.46 |
| Salicylic acid | 0 | 2.0 | 0 | 0 | 2.0 | 2.0 | 0.0 | 0.0 | 0.0 |
| 5-Chlorosalicylic acid | 0 | 0 | 2.0 | 0 | 0 | 0 | 2.0 | 2.0 | 1.0 |
| 2,4-Dihydroxybenzoic acid | 0 | 0 | 0 | 2.0 | 0.15 | 0.15 | 0.15 | 0.15 | 0.15 |
| Oleic acid | 0 | 0 | 0 | 0 | 0 | 0.25 | 0 | 0.25 | 0 |
| 2-Hexyl-1-decanol | 0 | 0 | 0 | 0 | 0 | 0.25 | 0 | 0.25 | 5 |
| Isostearyl Isostearate | 0 | 0 | 0 | 0 | 0 | 0 | 0 | 0 | 2 |
| Final pH | 4.2 | 4.2 | 4.2 | 4.2 | 4.2 | 4.2 | 4.2 | 4.2 | 4.2 |
| % Water Reduction versus Leave-on Treatment Control at dose of 0.10 g of composition for 1.0 g of hair | '— | — | — | — | 4 | 5 | 5 | 7 | 4 |
| % Water Reduction versus Leave-on Treatment Control at dose of 0.50 g of composition for 1.0 g of hair. Control is dosed at 0.50 g of composition for 1.0 g of hair | — | 4 | 5 | 5 | 9 | 8 | 10 | 10 | 12 |
| Feel Rating Leave-on Treatment Control at dose of 0.10 g of composition for 1.0 g of hair | 1 | 1 | 2 | 2 | 2 | 3 | 2 | 4 | 4 |

TABLE 5-continued

Leave-on Treatment Formulation

| Raw Material | Formula Example | | | | | | | |
|---|---|---|---|---|---|---|---|---|
| | XXXXI | XXXXII | XXXXIII | XXXXIV | XXXXV | XXXXVI | XXXXVII | XXXXVIII |
| Distilled Water | QS | QS | QS | QS | QS | QS | QS | QS |
| Ethanol | 50.0 | 50.0 | 50.0 | 50.0 | 50.0 | 50.0 | 50.0 | 50.0 |
| 5-Chlorosalicylic acid | 1.0 | | | 1.0 | 1.0 | 1.0 | | 2 |
| 2-Hexyl-1-decanol | | | 5.0 | 5.0 | | 5.0 | | |
| Isostearyl Isostearate | | 2.0 | | | 2.0 | 2.0 | | |
| Glyoxylic acid | | | | | | | 2 | 2 |
| Final pH | 4 | 4 | 4 | 4 | 4 | 4 | 4 | 4 |
| % Water Reduction versus Leave-on Treatment Control at dose of 0.10 g of composition for 1.0 g of hair | 1.3 | 0.7 | 1.0 | 2.0 | 1.4 | 3.0 | 1.0 | 1.0 |
| Feel Rating (on 5 scale point with 5 as highest and 1 as lowest) | 1 | 2 | 2 | 3 | 3 | 4 | 3 | 3 |

Results:

Formula XXXIII-XXXXVIII showed % water reduction at high humidity. Higher % water reductions are observed in hair treated with higher doses of leave-on Formulas XXXIII-XXXXVIII.

The feel assessment results indicate that combinations of
(d) 5-Chlorosalicylic acid and 2-hexyl-1-decanol;
(e) 5-Chlorosalicylic acid and isostearyl isostearate;
(f) 5-Chlorosalicylic acid and 2-hexyl-1-decanol and isostearyl isostearate provide, not only water absorption reduction (resulting in frizz benefit), but also tactile feel benefit. This is shown by the feel comparisons of (a) Example XXXXI versus Examples XXXXII and XXXXIII, (b) Example XXXXIII versus Examples XXXXIV and XXXXV, and (c) Example XXXXVI versus Examples XXXXVIII and XXXXVII (d) Example XXXXI versus Examples XXXXV, XXXXVI, XXXXVII and XXXIII Additional Evaluations Additional leave-on treatment compositions are prepared (Tables 6 and 7) according to the procedure described above, which are used to treat hair switches using the procedure described above (amount of 0.10 g of composition per g of hair). The switch is kept at high humidity (above 85%) for 2 hours. Then, ten experts are asked to rate each hair switch in terms of frizz, clean feel, and greasy feel, based on a 5 point scale, 5 being the highest and 1 being the lowest rating. Acceptable values are:

For frizz, less than 2 (lower number corresponds to less frizz);

For no greasy feel less than 3, (lower number corresponds to less greasy feel), and For clean feel greater than 3 (higher number corresponds to cleaner feel).

TABLE 6

Class I Compounds

| Raw Material | Formula Example | | | | | |
|---|---|---|---|---|---|---|
| | Control | XXXXIX | XXXXX | XXXXXI | XXXXXII | XXXXXIII |
| Distilled Water | 50.0% | 49.5% | 49.5% | 49.5% | 49.5% | 49.5% |
| Ethanol | 50.0% | 49.5% | 49.5% | 49.5% | 49.5% | 49.5% |
| 5-Chlorosalicylic acid | 0% | 1% | 0% | 0% | 0% | 0% |
| Salicylic acid | 0% | 0% | 1% | 0% | 0% | 0% |
| 4-Hydroxybenzenesulphonic acid | 0% | 0% | 0% | 1% | 0% | 0% |
| 2,4-Dihydroxybenzoic acid | 0% | 0% | 0% | 0% | 1% | 0% |
| Terminal Amino Silicone | 0% | 0% | 0% | 0% | 0% | 1% |
| Composition pH adjusted to | 4.2 | 4.2 | 4.2 | 4.2 | 4.2 | 4.2 |
| Greasy Feel | 2 | 1 | 2 | 2 | 2 | 4 |
| Frizz | 4 | 2 | 1 | 2 | 2 | 3 |
| Clean Feel | 4 | 4 | 3 | 4 | 4 | 1 |

Results of Hair Switch Rating from Class I Molecules:

Molecules (5-chlorosalicylic acid, salicylic acid, 4-hydroxybenzenesulphonic acid, 2,4-dihydroxybenzoic acid) from Class I provide hair benefits. More specifically, Table 1 shows that hair treatments with 5-chlorosalicyclic acid, salicylic acid, 4-hydroxybenzenesulfonic acid and 2,4-dihydroxybenzoic acid provide fizz protection with clean feel and without greasy feel negative, as opposed to treatment with terminal aminosilicone, which provide some frizz benefit but with greasy feel negative and significantly less clean feel.

TABLE 7

Class II Compounds

| Raw Material | Control | Formula Example | | | | |
|---|---|---|---|---|---|---|
| | | XXXXXIV | XXXXXV | XXXXXVI | XXXXXVII | XXXXXVIII |
| Distilled Water | 50.0% | 49.5% | 49.5% | 49.5% | 49.5% | 49.5% |
| Ethanol | 50.0% | 49.5% | 49.5% | 49.5% | 49.5% | 49.5% |
| Isostearyl isostearate | 0% | 1% | 0% | 0% | 0% | 0% |
| 2-Hydroxyethyl salicylate | 0% | 0% | 1% | 0% | 0% | 0% |
| Octyl salicylate | 0% | 0% | 0% | 1% | 0% | 0% |
| 2-Hexyl-1-decanol | 0% | 0% | 0% | 0% | 1% | 0% |
| Terminal Amino Silicone | 0% | 0% | 0% | 0% | 0% | 1% |
| Composition pH adjusted to | 4.2 | 4.2 | 4.2 | 4.2 | 4.2 | 4.2 |
| Greasy Feel | 2 | 2 | 2 | 2 | 3 | 4 |
| Frizz | 4 | 2 | 2 | 1 | 1 | 3 |
| Clean Feel | 4 | 3 | 3 | 3 | 3 | 1 |

Results of Hair Switch Rating from Class II Molecules:

Molecules (Isostearyl isostearate, 2-hydroxylethyl salicylate, octyl salicylate, 2-hexyl-1-decanol) from Class II provide hair benefits. More specifically, Table 2 shows that hair treatment with isostearyl isostearate, 2-hydroxyethyl salicylate, octyl salicylate, and 3-hexyl-1-decanol provide frizz protection with clean feel and without greasy feel negative, as opposed to treatment with terminal aminosilicone, which provide some frizz benefit but with greasy feel negative and significantly less clean feel.

Evaluation of Hair Friction

Leave-on formulation containing Moisture Control Material and Silicone oil shows improvement in dry feel compared to untreated hair. This is concluded by measurement of dry hair friction. For this evaluation, natural virgin brown hair switches (4.0 g) are washed with clarifying shampoo, and then treated with leave-on treatment of composition XXXXXIX according to the protocol described above. Before the evaluation, the switches are air dried overnight in a controlled temperature and humidity room (22° C./50% RH). The friction force (grams) between the hair surface and a urethane pad along the hair is measured, with three measurements per switch using an Instron Tester instrument (Instron 5542, Instron, Inc, Canton, Mass., USA).

TABLE 8

Hair Friction

| Raw Material | Formula Example XXXXXIX | Control Hair - No Treatment |
|---|---|---|
| Distilled Water | 49.5% | |
| Ethanol | 49.5% | |
| 2,4 dihydroxybenzoic acid | 1% | |
| Silicone oil | 0% | |
| Composition pH adjusted to | 4.2 | |
| Average Force (g) | 40 | 55 |

As Table 8 indicates, treatment of hair with leave-on composition containing Moisture Control material and silicone oil results in reduced hair friction, which indicates improved dry feel.

It is known that organic hydrophobic molecules that are naturally present inside the hair (e.g. as part of Cell Membrane Complex lipids) contribute to its strength and integrity. It is also known that cosmetic treatments, such as oxidative coloring and permanent shaping result in reduction of the concentration of such hydrophobic material from hair. Thus, penetration of hydrophobic materials (e.g. Class II materials) inside the hair can contribute to lipid replenishment, which, at the same time, reduces water uptake to deliver moisture or frizz control benefit. Combination of different Class II materials e.g. benzyl alcohol, 2-hexyl-1-decanol, isostearyl isostearate, have multi-functionality of penetration, getting embedded into lipid of hair and also increasing the penetration of other hydrophobic materials like oleic resulting in further increase hydrophobicity of the hair interior.

Leave On Composition Containing Gel Matrix Preparation:

One of Example of the leave on formulation compositions can be prepared by any conventional method well known in the art containing gel matrix. The cationic surfactants and the fatty alcohols are mixed together and heated to from about 66° C. to about 85° C. to form an oil phase. Separately, the disodium EDTA, the Methylchloroisothiazolinone (preservative) and the water are mixed and heated to from about 20° C. to about 48° C. to form an aqueous phase. The oil phase is mixed into the water phase under high shear to form the gel matrix. The remaining of the components are added into the gel matrix with agitation. Then, the composition is cooled down to room temperature.

TABLE 9

Moisture control materials in leave on formulation containing Gel Matrix

| Raw Material | Active % | Formula Example | |
|---|---|---|---|
| | | XXXXXX (wt./wt.)% | XXXXXXI (wt./wt.)% |
| Hydroxyethyl cellulose[1] | 80 | 0.400 | 0.400 |
| Cetyl Alcohol[2] | 90 | 0.575 | 0.575 |
| Stearyl Alcohol[3] | 97 | 0.383 | 0.383 |
| Benzyl Alcohol[4] | 99 | 0.400 | 0.400 |
| Disodium EDTA, Dihydrate[5] | 99 | 0.127 | 0.127 |

TABLE 9-continued

Moisture control materials in leave on formulation containing Gel Matrix

| | | Formula Example | |
|---|---|---|---|
| Raw Material | Active % | XXXXXX (wt./wt.)% | XXXXXXI (wt./wt.)% |
| Glyceryl monostearate (PoloxWSR N-10)[6] | 1.5 | 0.299 | 0.299 |
| Terminal Amino Silicone[7] | 90-100 | 2 | 2 |
| Perfume | | 0.550 | 0.550 |
| Salicylic acid[8] | 99.5 | 0 | 2.0 |
| Isostearyl Isostearate[11] | 100 | 0 | 1.0 |
| 2-hexyldecanol[12] | 97 | 0 | 5.0 |
| Purified Water | | Q.S. | Q.S. |
| % Water Reduction versus XIV (control) at dose of 0.1 g of composition for 1 g of hair | | — | 4 |
| pH | | 5.2 | 5.2 |
| % Frizz Reduction | | | 20 |

[1]Natrosol ™ hydroxyethylcellulose Supplied by Ashland (Kentucky, US)
[2]Supplied by P&G Chemicals
[3]Supplied by P&G Chemicals
[4]Supplied by Ineos Maastricht BV (Maastricht NL)
[5]Trilon BD Powder supplied by BASF SE (Ludwigshafen, DE)
[6]POLYOX ™ WSR N-10 (Glyceryl monostearate) supplied by Dow chemicals (Michigan US)
[7]Y-14945 supplied by Momentive Performance Materials
[8]Supplied by API Corpotration
[9]Supplied by Sigma Aldrich
[10]Supplied by Sigma Aldrich
[11]Crodamol ISIS supplied by Croda
[12]Isofol 16 supplied by Sasol (Brunsbuettel, DE)

Results:

Hair Switches treated with leave on treatment of example XXXXXXI, using the leave on hair treatment protocol described in page 45, shows % water reduction by DVS method of 4% vs hair treated with example XXXXXX control.

TABLE 10

Regimen Examples

| Regimen Steps | Regimen Example 1 | Regimen Example 2 | Regimen Example 3 | Regimen Example 4 | Regimen Example 5 | Regimen Example 6 |
|---|---|---|---|---|---|---|
| Step 1 | Shampoo | Deep Conditioning Treatment*/Soaking# | Shampoo | Shampoo | Shampoo | Shampoo |
| Step 2 | Deep Conditioning Treatment*/Soaking# | Shampoo | Deep Conditioning Treatment*/Soaking# | Conditioner | Deep Conditioning Treatment*/Soaking# | Leave-on |
| Step 3 | Conditioner | Conditioner | Leave-on | Leave-on | | |
| Step 4 | Leave-on | Leave-on | | | | |

*Deep Conditioning Treatment Time (T) and Dosage (D) may vary from regimen to regimen
Soaking Time may vary from regimen to regimen

TABLE 11

Different Regimen Steps Examples

| Regimen Steps | Control Regimen | Regimen Example 7 | Regimen Example 8 | Regimen Example 9 | Regimen Example 10 | Regimen Example 11 | Regimen Example 12 |
|---|---|---|---|---|---|---|---|
| Step 1 | Shampoo Control A | Shampoo Example II | Deep Conditioning Treatment Example XVIII | Shampoo Example II | Shampoo Example II | Shampoo Example II | Shampoo Example II |
| Step 2 | Deep Conditioning Treatment Control A | Deep conditioning Treatment Example XVIII | Shampoo Example II | Deep conditioning Treatment Example XVIII | Rinse off Conditioner Example X | Deep conditioning Treatment Example XVIII | Leave-on treatment Example XXXIV |
| Step 3 | Rinse off Conditioner Control A | Rinse off Conditioner Example X | Rinse off Conditioner Example X | Leave-on treatment Example XXXIV | Leave-on treatment Example XXXIV | | |
| Step 4 | Leave-on treatment control A | Leave-on treatment Example XXXIV | Leave-on treatment Example XXXIV | | | | |

TABLE 11-continued

Different Regimen Steps Examples

| Regimen Steps | Control Regimen | Regimen Example 7 | Regimen Example 8 | Regimen Example 9 | Regimen Example 10 | Regimen Example 11 | Regimen Example 12 |
|---|---|---|---|---|---|---|---|
| % Water reduction vs Control Regimen | 0 | 8 | 6 | 7 | 5 | 4 | 2.5 |

Results:

Above Table 11 shows when regimen steps are applied to hair in different steps order of treatment, this results in difference in % water reduction. This is driven mainly by step 2 deep conditioning treatment which is applied after shampoo as in example 7 where it is allowed to stay on hair longer so that moisture control material penetrates more. This is followed by rinse off conditioner, and leave on which further increase active inside hair. It is seen regimen example 7 shows higher % water reduction than example 8 to 12.

TABLE 12

Varying Treatment Time and Dosage of Deep Conditioning Treatment Step in Regimen Example 1 (wherein, Shampoo Example III → Deep Conditioning Treatment Example XXIII → Conditioner Example XV → Leave on treatment Example XXXXX)

| | Regimen Example 1 | | | |
|---|---|---|---|---|
| | Regimen Example 1A | Regimen Example 1B | Regimen Example 1C | Regimen Example 1D |
| Treatment Time (T) (minutes) - refer Deep Conditioning Treatment Protocol | 20 | 10 | 20 | 20 |
| Dosage (D) (g of treatment per g of hair) - refer Deep Conditioning Treatment Protocol | 0.2 | 0.5 | 0.5 | 1 |
| % Water Reduction versus Control | 6 | 9 | 9 | 9 |

Results: In this regimen testing example 1 (mentioned in table 12), we changed the treatment and dosage time at step 2 deep conditioning treatment, keeping the rest of steps same. We found that minimum amount of treatment time (T) is 10 mins and minimum dosage (D) is 0.5 g/g (0.5 g of deep conditioning treatment to 1 g of hair) to get the maximum frizz control benefit. We also found as we increase the dosage of treatment, amount of active penetration increase inside the hair, resulting in increase in % water reduction, leading to higher frizz control.

TABLE 13

Retention of Moisture Control Materials inside Hair after multiple washes with Shampoo Control A

| | | | | | | % water reduction | | | |
|---|---|---|---|---|---|---|---|---|---|
| | | Shampoo | Deep Conditioning Treatment (D: 0.5 g/g, T: 10 min) | Rinse off Conditioner | Leave on | After 1 time treatment | After 5 times treatment | After 5 times Shampoo Control A wash | After 10 times shampoo control A wash |
| Leg A | | Shampoo Example VIII | Example XXIII | Example XVI | Example XXXXVI | 9 | 20 | 14 | 9 |
| Leg B | | Shampoo Example II | Example XVIII | Example X | Example XXXIV | 7 | — | 3 | — |
| Leg C | | Shampoo Control A | Example XXV | Conditioner Control A | XXXVIII | 4 | 3.5 | — | — |

Results: From Above data in table 13, it shows on multiple numbers of washes with formulation containing the moisture control materials in a regimen process, high amount of moisture control material penetrates inside the hair resulting in increase in % water reduction. It is also found that high amount of moisture control material which penetrates inside the hair after multiple washes has high retention as after washing with shampoo without moisture control material even after 5 and 10 times, it has slight drop in % water reduction from 20% to 14% and 9% respectively. This suggests that moisture control materials have high retention inside the hair and will show efficacy even after multiple washes with formulation containing no moisture control material.

TABLE 14

Addition of Moisture Control Materials in multiple steps of Regimen Example 1:

| | Regimen Example | | | | |
|---|---|---|---|---|---|
| | Control | Example 13 | Example 14 | Example 15 | Example 16 |
| Shampoo Example | Shampoo Control A | Example II | Example II | Example II | Example II |
| Deep Conditioning Treatment/ Soaking Example | Deep Conditioning Treatment Control A | Deep Conditioning Treatment Control A | Deep Conditioning Treatment Control A | Example XVIII | Example XVIII |
| Rinse off Conditioner Example | Rinse off Conditioner Control A | Rinse off Conditioner Control A | Example X | Example X | Example X |
| Leave on Treatment Example | Leave on Treatment Control A | Leave on Treatment Control A | Leave on Treatment Control A | Leave on Treatment Control | Example XXXIV |
| Amount of 5-Chloro Salicylic acid (mg) penetration inside per g of hair | 0 | 0.4 | 0.6 | 1.6 | 3.1 |

In above table 14, addition of moisture control material to each step of regimen is evaluated. It is found that addition of moisture control material to each step, increases the penetration of active inside hair and increase in % water reduction resulting in higher frizz control. Hence, if the moisture control material is used in all steps of regimen rather than 1 step, then it would be higher benefit in 1 cycle itself.

TABLE 15

Example of Addition of single variable moisture control material in all steps of Regimen Example 1

| | Regimen Example | | | | |
|---|---|---|---|---|---|
| | Control Regimen | Regimen Example 17 | Regimen Example 18 | Regimen Example 19 | Regimen Example 20 |
| Shampoo Example (dose 0.2 g per g of hair) | Shampoo Control A | Example III | Example V | Example IV | Example II |
| Deep Conditioning Treatment (dose 0.2 g per g of hair, 15 mins) | Deep Conditioning Treatment Control A | Example XIX | Example XXI | Example XX | Example XVIII |
| Rinse off Conditioner (dose 0.2 g per g of hair) | Rinse off Conditioner Control A | Example XI | Example XIII | Example XII | Example X |
| Leave on treatment (dose 0.1 g per g of hair) | Leave on treatment control A | Example XXXIV | Example XXXXIII | Example XXXXII | Example XXXXI |
| % Water Reduction versus Control | 0 | 1.8 | 1.1 | 0.9 | 3.7 |

In above table 15, it shows addition of moisture control material in all steps of regimen results in increase in % water reduction, delivering higher frizz control benefit.

TABLE 16

Addition of Glyoxylic acid at
Deep Conditioning Treatment Step and Leave on Step

|  | Control Regimen | Regimen Example 2 | | |
|---|---|---|---|---|
|  |  | Example 21 | Example 22 | Example 23 |
| Deep Conditioning Treatment Example | Deep Conditioning Treatment Control | XXII | XXIV | XXV |
| Shampoo Example | Shampoo Control | II | II | II |
| Rinse off Conditioner Example | Rinse off Conditioner Control | X | X | X |
| Leave on Treatment Example | Leave on Treatment Control | XXXVIII | XXXIX | XXXX |
| % water reduction vs control | 0 | 6.5 | 2 | 8.0 |

In above table 16, we added glyoxylic acid at deep conditioning treatment, glyoxylic acid is showing additive benefit to moisture control materials. Addition of glyoxylic acid further increase % water reduction, hence increase frizz control benefit.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the hair care composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of Embodiments of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for hair frizz reduction comprising the steps of:
    (a) performing a hair cleansing by applying to the hair a shampoo composition and rinsing the shampoo composition from the hair with water;
    (b) performing one or more additional hair treatment steps selected from the group consisting of:
        (1) a rinse-off conditioning treatment using a rinse-off conditioner composition;
        (2) a soaking treatment using a soaking treatment composition;
        (3) a deep conditioning treatment using a deep conditioning treatment composition; and
        (4) a leave-on treatment using a leave-on treatment composition;
    wherein the step (a) is performed before the step (b),
    wherein the (b)(4) leave-on treatment, if present in the method, is performed as the last step after all the other treatments,
    wherein the shampoo composition used in the step (a) and at least one of the composition used in the step (b) comprise from about 0.1 to about 20% of moisture control material, wherein the moisture control material comprises salicylic acid and/or 5-chlorosalicylic acid, in combination with at least one of 2,4-dihydroxybenzoic acid, isostearyl isostearate, and 2-hexyl-1-decanol, in which the said salicylic acid and/or 5-chlorosalicylic acid have a % protein binding higher than 20, molecular volume lower than 500, partition coefficient octanol to water (log P) lower than 3 and hydrogen binding higher than 10 and pKa lower than 5.0, and the said isostearyl isostearate and 2-hexyl-1-decanol have protein binding higher than 10, molecular volume lower than 1500, log P higher than 0.5 and pKa of 5 or higher and hydrogen-binding higher than 4,
    wherein hair treated with the method for hair frizz reduction absorbs moisture at least 2% less than hair treated with the corresponding combination of treatments using compositions having no the moisture control material, and
    wherein the moisture absorption is measured using DVS method.

2. The method of claim 1, wherein the additional hair treatment comprises the (b)(1) rinse-off conditioning treatment using the rinse-off conditioner composition, wherein the shampoo composition and the rinse-off conditioning composition comprise from about 0.1 to about 20% of the moisture control material.

3. The method of claim 1, wherein the additional hair treatment comprises the (b)(3) deep conditioning treatment using the deep conditioning treatment composition, wherein the shampoo composition and the deep conditioning treatment composition comprise from about 0.1 to about 20% of the moisture control material.

4. The method of claim 1, wherein the additional hair treatment comprises the (b)(4) leave-on treatment using the leave-on treatment composition, wherein the shampoo composition and the leave-on treatment composition comprise from about 0.1 to about 20% of the moisture control material.

5. The method of claim 2, wherein the method also comprises the (b)(3) deep conditioning treatment using the deep conditioning treatment composition, wherein the (b)(3) deep conditioning treatment is performed after the (b)(1) rinse-off conditioning treatment, and wherein the shampoo composition, the rinse-off conditioning composition and the deep conditioning treatment composition comprise from about 0.1 to about 20% of the moisture control material.

6. The method of claim 2, wherein the method also comprises the (b)(4) leave-on treatment using the leave-on treatment composition, wherein the shampoo composition, the rinse-off conditioning composition and the leave-on treatment composition comprise from about 0.1 to about 20% of the moisture control material.

7. The method of claim 5, wherein the method also comprises the (b)(4) leave-on treatment using the leave-on treatment composition, wherein the shampoo composition, the rinse-off conditioning composition, the deep conditioning treatment composition and the leave-on treatment composition comprise from about 0.1 to about 20% of the moisture control material.

8. The method of claim 3, wherein the method also comprises the (b)(1) rinse-off conditioning treatment using the rinse-off conditioning composition, wherein the (b)(1) rinse-off conditioner treatment is performed after the (b)(3) deep conditioning treatment, and wherein the shampoo composition, the deep conditioning treatment composition, and the rinse-off conditioning composition comprise from about 0.1 to about 20% of the moisture control material.

9. The method of claim 8, wherein the method also comprises the (b)(4) leave-on treatment using the leave-on treatment composition, wherein the shampoo composition, the deep conditioning treatment composition, the rinse-off conditioning composition, and the leave-on treatment composition comprise from about 0.1 to about 20% of the moisture control material.

10. The method of claim 1, wherein the additional hair treatment steps comprise the (b)(1) rinse-off conditioning treatment using the rinse-off conditioning composition, the (b)(3) deep conditioning treatment using the deep conditioning treatment composition, and the (b)(4) leave-on treatment using the leave-on treatment composition, wherein the (b)(3) deep conditioning treatment is performed after the (b)(1) rinse-off conditioning treatment, and wherein the rinse-off conditioning composition, the deep conditioning treatment composition, and the leave-on treatment composition comprise from about 0.1 to about 20% of the moisture control material.

11. The method of claim 1, wherein the additional hair treatment steps comprise the (b)(1) rinse-off conditioning treatment using the rinse-off conditioning composition, the (b)(3) deep conditioning treatment using the deep conditioning treatment composition, and the (b)(4) leave-on treatment using the leave-on treatment composition, wherein the (b)(1) rinse-off conditioning treatment is performed after the (b)(3) deep conditioning treatment, and wherein the deep conditioning treatment composition and the leave-on treatment composition comprise from about 0.1 to about 20% of the moisture control material, and further wherein the leave-on treatment composition does not contain the said moisture control material.

12. The method of claim 1, wherein the additional hair treatment steps comprise the (b)(3) deep conditioning treatment using the deep conditioning treatment composition, and the (b)(4) leave-on treatment using the leave-on treatment composition, wherein the deep conditioning treatment composition and the leave-on treatment composition comprise from about 0.1 to about 20% of the moisture control material.

13. The method of claim 3, wherein the method also comprises the (b)(4) leave-on treatment using the leave-on treatment composition, wherein the shampoo composition, and the deep conditioning treatment composition comprise from about 0.1 to about 20% of the moisture control material, and wherein the leave-on treatment composition does not contain the said moisture control material.

14. The method of claim 3, wherein the method also comprises the (b)(4) leave-on treatment using the leave-on treatment composition, wherein the shampoo composition, the deep conditioning treatment composition and the leave-on treatment composition comprise from about 0.1 to about 20% of the moisture control material.

15. The method of claim 1, wherein the additional hair treatment steps comprise the (b)(3) deep conditioning treatment using the deep conditioning treatment composition, and the (b)(4) leave-on treatment using the leave-on treatment composition, wherein the deep conditioning treatment composition and the leave-on treatment composition comprise from about 0.1 to about 20% of the moisture control material.

16. The method of claim 2, wherein the additional hair treatment steps comprise the (b)(4) leave-on treatment using the leave-on treatment composition, wherein the shampoo composition, the rinse-off composition, and the leave-on treatment composition comprise from about 0.1 to about 20% of the moisture control material.

17. The method of claim 2, wherein the additional hair treatment steps comprise the (b)(4) leave-on treatment using the leave-on treatment composition, wherein the shampoo composition and the rinse-off composition comprise from about 0.1 to about 20% of the moisture control material, and further wherein the leave-on treatment composition does not contain the said moisture control material.

18. The method of claim 1, wherein the additional hair treatment steps comprise the (b)(3) deep conditioning treatment using the deep conditioning treatment composition and the (b)(4) leave-on treatment using the leave-on treatment composition, wherein the shampoo composition, and the leave-on treatment comprise from about 0.1 to about 20% of the moisture control material, and further wherein the deep conditioning treatment composition does not contain the said moisture control material.

19. The method of claim 1, wherein the (b)(3) deep conditioning treatment comprises a deep conditioning treatment A using a deep conditioner treatment composition A, and a deep conditioning treatment B using a deep conditioning treatment composition B, wherein the deep conditioning treatment A is performed before the deep conditioning treatment B, and wherein the shampoo composition and the deep conditioning treatment composition A comprise from about 0.1 to about 20% of the moisture control material, and further wherein the deep conditioning treatment composition B does not contain the said moisture control material.

20. The method of claim 19, wherein the method also comprises the (b)(4) leave-on treatment using the leave-on treatment composition, wherein the shampoo composition and the deep conditioning treatment composition A comprise from about 0.1 to about 20% of the moisture control material, and further wherein the deep conditioning treatment composition B and the leave-on treatment composition do not contain the said moisture control material.

21. The method of claim 19, wherein the method also comprises the (b)(4) leave-on treatment using the leave-on treatment composition, wherein the shampoo composition, the deep conditioning treatment composition A and the leave-on treatment composition comprise from about 0.1 to about 20% of the moisture control material, and further wherein the deep conditioning treatment composition B does not contain the said moisture control material.

22. The method of claim 1, wherein the (b)(3) deep conditioning treatment comprises a first deep conditioning treatment using a first deep conditioning treatment composition, and a second deep conditioning treatment using a second deep conditioning treatment composition and the (b)(4) leave-on treatment using the leave-on treatment composition, wherein the first deep conditioning treatment is performed before the second deep conditioning treatment, and wherein the first deep conditioning treatment composition and the leave-on treatment composition comprise from about 0.1 to about 20% of the moisture control material, and further wherein the second deep conditioning treatment composition does not contain the said moisture control material.

23. The method of claim 1, wherein the (b)(3) deep conditioning treatment is replaced by the (b)(2) soaking treatment using the soaking treatment composition.

24. The method of claim 1, wherein the additional hair treatment steps comprise the (b)(1) rinse-off conditioning treatment using the rinse-off conditioning composition, the (b)(2) soaking treatment using the soaking treatment composition, and the (b)(4) leave-on treatment using the leave-on treatment composition, wherein the (b)(2) soaking treatment is performed after the (b)(1) rinse-off conditioning treatment, and wherein the shampoo composition and the soaking treatment composition comprise from about 0.1 to about 20% of the moisture control material, and further wherein the rinse-off conditioning composition and the leave-on treatment composition do not contain the said moisture control material.

25. The method of claim 1, wherein the additional hair treatment steps comprise the (b)(1) rinse-off conditioning treatment using the rinse-off conditioning composition, the (b)(2) soaking treatment using the soaking treatment composition, and the (b)(4) leave-on treatment using the leave-on treatment composition, wherein the (b)(2) soaking treatment is performed after the (b)(1) rinse-off conditioning treatment, and wherein the rinse-off conditioning composition and the leave-on treatment composition comprise from about 0.1 to about 20% of the moisture control material, and further wherein the soaking treatment composition does not contain the said moisture control material.

26. The method of claim 1, wherein the additional hair treatment steps comprise the (b)(1) rinse-off conditioning treatment using the rinse-off conditioning composition, the (b)(2) soaking treatment using the soaking treatment composition, and the (b)(4) leave-on treatment using the leave-on treatment composition, wherein the (b)(2) soaking treatment is performed after the (b)(1) rinse-off conditioning treatment, and wherein the soaking treatment composition and the leave-on treatment composition comprise from about 0.1 to about 20% of the moisture control material, and further wherein the rinse-off conditioning composition does not contain the said moisture control material.

27. The method of claim 1, wherein the additional hair treatment steps comprise the (b)(1) rinse-off conditioning treatment using the rinse-off conditioning composition, the (b)(2) soaking treatment using the soaking treatment composition, and the (b)(4) leave-on treatment using the leave-on treatment composition, wherein the (b)(2) soaking treatment is performed after the (b)(1) rinse-off conditioning treatment, and wherein the shampoo composition, the soaking treatment composition, and the leave-on treatment composition comprise from about 0.1 to about 20% of the moisture control material, and further wherein the rinse-off conditioning composition does not contain the said moisture control material.

28. The method of claim 1, wherein the additional hair treatment steps comprise the (b)(2) soaking treatment using the soaking treatment composition, and the (b)(4) leave-on treatment using the leave-on treatment composition, wherein the soaking treatment composition and the leave-on treatment composition comprise from about 0.1 to about 20% of the moisture control material.

29. The method of claim 1, wherein the moisture control material is salicylic acid or 5-chlorosalicylic acid, in combination with at least one of 2,4-dihydroxybenzoic acid, isostearyl isostearate and 2-hexyl-1-decanol.

30. The method of claim 1, wherein the moisture control material is salicylic acid or 5-chlorosalicylic acid, in combination with 2,4-dihydroxybenzoic acid.

31. The method of claim 1, wherein the moisture control material is salicylic acid or 5-chlorosalicylic acid, in combination with at least one of 2-hexyl-1-decanol and 2,4-dihydroxybenzoic acid.

* * * * *